(12) United States Patent
Wang et al.

(10) Patent No.: US 8,461,165 B2
(45) Date of Patent: Jun. 11, 2013

(54) 2-SUBSTITUTED PHENYL-5,7-DIHYDROCARBYL-3,7-DIHYDROPYRROLO[2,3-D] PYRIMIDIN-4-ONE DERIVATIVES, THE PREPARATION AND THE PHARMACEUTICAL USE THEREOF

(75) Inventors: Yongfeng Wang, Tianjin (CN); Kejun Zhao, Shandong (CN)

(73) Assignees: Yangtze River Pharmaceutical (Group) Co., Ltd, Taizhou (CN); Tianjin North Pharma Sci-Tech Co., Ltd, Tianjin (CN)

(*) Notice: Subject to any disclaimer, the term of this patent is extended or adjusted under 35 U.S.C. 154(b) by 517 days.

(21) Appl. No.: 12/685,376

(22) Filed: Jan. 11, 2010

(65) Prior Publication Data

US 2010/0204223 A1    Aug. 12, 2010

Related U.S. Application Data

(62) Division of application No. 12/043,700, filed on Mar. 6, 2008, now Pat. No. 7,741,483, which is a division of application No. 10/559,516, filed as application No. PCT/CN2004/000487 on May 14, 2004, now Pat. No. 7,745,433.

(30) Foreign Application Priority Data

Jun. 6, 2003 (CN) .................................. 03142399

(51) Int. Cl.
- *A61K 31/519* (2006.01)
- *A61P 15/10* (2006.01)
- *A61P 9/12* (2006.01)
- *C07D 487/04* (2006.01)

(52) U.S. Cl.
USPC ..... 514/265.1; 544/280; 544/117; 514/234.2; 514/252.16

(58) Field of Classification Search
USPC .................................. 544/280; 514/265.1
See application file for complete search history.

(56) References Cited

U.S. PATENT DOCUMENTS 6,407,114 B1    6/2002  Bunnage et al.

FOREIGN PATENT DOCUMENTS

| EG | 2001060607 A1 | 6/2001 |
| EP | 1 092 718 A1 | 4/2001 |
| IN | 186584 A | 3/1999 |
| JP | 10316654 A | 12/1998 |
| JP | 2000128884 A | 5/2000 |
| WO | 9616657 A1 | 6/1996 |
| WO | 0064424 A2 | 11/2000 |
| WO | 0160825 A1 | 8/2001 |
| WO | 0200659 A2 | 1/2002 |
| WO | 02074774 A1 | 9/2002 |

OTHER PUBLICATIONS

Boswell-Smith et al. (Br. J. Pharmacol., Phosphodiesterase Inhibitors, 2006, 147(S1): s252-257).*
Neidle, Stephen, ed. (Cancer Drug Design and Discovery, Elsevier/Academic Press, 2008, pp. 427-431).*
Rotella, D. (Nature, 2002, 1, pp. 674-682).*
R. Mattson, et al., Selective N-1-Methylation of 2-Aminopyrroles with Sodium Hydride and Dimethyl Sulfate, Division of Medicinal Chemistry, College of Pharmacy, University of South Carolina, Columbia, South Carolina 29, 208, U.S.A., 1979, (3), 217-218.
H. Pichler, et al., Synthese von 7-unsubstituierten 7H-Pyrrolo [2,3-d]-pyrimidinen, Liebigs Ann. Chem., 1986, 9, 1485-1505.
K. Eger, et al., Synthesis of Pyrrolo [2,3-d] pyrimidine Ribosides and their Potential in Chemotherapeutics, J. Heterocyclic Chem., 1990, 27(7), 2069-2075.
D. Rotella, et al., Optimization of Substituted N-3-Benzylimidazoquinazolinone Sulfonamides as Potent and Selective PDE5 Inhibitors, J. Med. Chem. 2000, 43(26), 5037-5043.
S. Jing, et al., Synthesis of Sildenafil, Chinese Academy of Medical Sciences, 1999, 9(3) pp. 220-222.

* cited by examiner

*Primary Examiner* — Susanna Moore
(74) *Attorney, Agent, or Firm* — Pergament Gilman & Cepeda LLP; Edward D. Pergament; Milagros A. Cepeda

(57) ABSTRACT

The invention relates to the compounds of formula I, their preparation and the pharmaceutical compositions containing the compounds. The invention also relates to the use of the compounds of formula I in preparing medicines, which can treat sexual dysfunction of animals including human (male and female), especially erectile dysfunction of male and the diseases in which the function of phospholipase 5 (cGMP PDE5) is involved.

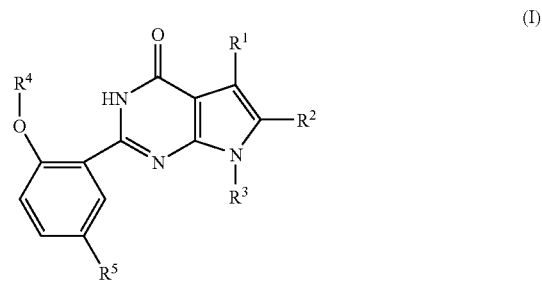

(I)

1 Claim, No Drawings

2-SUBSTITUTED PHENYL-5,7-DIHYDROCARBYL-3,7-DIHYDROPYRROLO[2,3-D] PYRIMIDIN-4-ONE DERIVATIVES, THE PREPARATION AND THE PHARMACEUTICAL USE THEREOF

CROSS REFERENCE TO RELATED APPLICATIONS

This application is a divisional application of U.S. patent application Ser. No. 12/043,700 filed Mar. 6, 2008, now U.S. Pat. No. 7,741,483, which is a divisional application of U.S. patent application Ser. No. 10/559,516 filed Dec. 6, 2005, now U.S. Pat. No. 7,745,433, which claims the benefit of International Application PCT/CN2004/000487, filed May 14, 2004, all of which are hereby incorporated herein by reference in their entireties.

FIELD OF INVENTION

The present invention relates to 2-substituted phenyl-5,7-dihydrocarbyl-3,7-dihydropyrrolo[2,3-d]pyrimidin-4-one derivatives, the process for their preparation, the composition containing them, and the use for treatment and/or prevention of sexual dysfunction and other diseases related to phospholipase 5.

BACKGROUND OF INVENTION

Sildenafil, disclosed in WO9428902, is first kind of orally-administrated potent inhibitors of phospholipase 5 in treatment of the erectile dysfunction of man. By inhibiting the phospholipase 5 in corpus cavernosum, it can achieve the purpose of relaxing smooth muscle in human corpus cavernosum, improving penile hyperemia so as to result in erection. The effective rates of sildenafil in treating male sexual organs erectile dysfunction amount to 80%.

Also, Pfizer Ltd. has developed a series of 1,6-dihydropyrrol[4,3-d]pyrimidin-7-one derivatives, and broadened their therapeutic area where such indications was thought to be treated by inhibiting phospholipase 5. All of these compounds are disclosed in EP0951098, WO9849116, U.S. Pat. No. 6,251,904, and WO0024745, and the latter two of patents include the compounds whose substituted phenyl on C-5 is replaced by the substituted pyridin-2-yl. On the basis of the structure of Sildenafil, DONG A PHARMA Co. Ltd. of Korea developed a series of mono substituted derivatives in the nitrogen atom of sulfonylamino group, as disclosed in WO0027848 and WO0198304. Presently, as described in WO0216364, in order to further enhance water-solubility, LG Chem. Invest. Ltd. disclosed the derivatives of 1,6-dihydropyrrolo[4,3-d]-pyrimidin-7-one with polyethylene glycol. In addition, 1,5-dihydropyrrolo[3,4-d]pyrimidin-4-ones and 1,9-dihydropurin-6-ones were developed by Pfizer Ltd. for the treatment of sexual dysfunction (U.S. Pat. No. 6,100,270). WO0160825 disclosed 3,5-dihydropyrrolo[3,2-d]pyrimidin-4-ones are useful for the treatment of impotence. Recently, 3H-imidazo[5,1-f][1,2,4]triazin-4-ones was disclosed by Bayer Co. Ltd. in the patent application DE19881732.

DETAILED DESCRIPTION OF THE INVENTION

The object of the present invention is to provide compounds for treatment of sexual dysfunction and other diseases related to phospholipase 5.

Thus, according to one aspect, the invention provides novel aryl substituted 3,7-dihydropyrrolo[2,3-d]pyrimidin-4-ones and their pharmaceutically acceptable salts (also named Yonkenafil), the compounds are the structure of general formula (I):

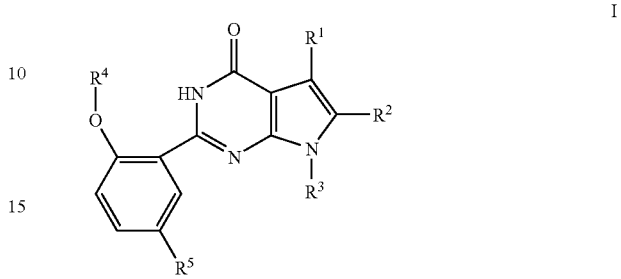

wherein $R^1$ is H; $C_1 \sim C_4$ branched or straight chain alkyl; $C_1 \sim C_4$ halogenated branched or straight chain alkyl; $C_2 \sim C_6$ alkenyl; $C_2$-$C_4$ alkynyl; pyridyl, pyrimidinyl imidazolyl; except H, the above substituents may be optionally substituted with one or more following groups: halogen, cyano, nitro, hydroxyl, carboxyl, guanidino, $C_1 \sim C_4$ alkyl, $C_1 \sim C_4$ alkoxyl, $C_1 \sim C_4$ alkanoyl, $C_3 \sim C_5$ cycloalkyl, substituted phenyl, substituted heterocyclic group, $CONR^5R^6$, $NR^5R^6$, $CO_2R^7$, $NHSO_2R^8$ or $SO_2NR^9R^{10}$;

$R^2$ is H; $C_1 \sim C_3$ branched or straight chain alkyl; $C_1 \sim C_3$ halogenated branched or straight chain alkyl; $C_2 \sim C_6$ alkenyl; $C_2 \sim C_4$ alkynyl; substituted phenyl; except H, the above substituents may be optionally substituted with one or more following groups: halogen, cyano-, nitro, hydroxyl, carboxyl, guanidino-, $C_1 \sim C_4$ alkyl, $C_1 \sim C_4$ alkoxyl, $C_1 \sim C_4$ alkanoyl, $C_3 \sim C_5$ cycloalkyl, substituted heterocyclic group, $CONR^6R^7$, $NR^6R^7$, $CO_2R^8$, $NHSO_2R^9$ or $SO_2NR^{10}R^{11}$;

$R^3$ is H; $C_1 \sim C_6$ branched or straight chain alkyl which may be optionally substituted with $C_3 \sim C_6$ cycloalkyl or $C_1 \sim C_4$ alkoxyl; $C_2 \sim C_4$ alkenyl; $C_2 \sim C_4$ alkynyl;

$R^4$ is H; $C_1 \sim C_6$ branched or straight chain alkyl which may be optionally substituted with $C_3 \sim C_6$ cycloalkyl or $C_1 \sim C_4$ alkoxyl; $C_2 \sim C_4$ alkenyl; $C_2 \sim C_4$ alkynyl;

$R^5$ is H; $C_1 \sim C_4$ branched or straight chain alkyl which may be optionally substituted with OH, $NR^6R^7$, CN, $CONR^6R^7$ or $CO_2R^8$; $C_2 \sim C_4$ alkenyl which may be optionally substituted with CN, $CONR^6R^7$ or $CO_2R^8$; $C_2 \sim C_4$ alkoxyl optionally substituted with $NR^6R^7$; ($C_2 \sim C_3$ alkoxyl) $C_1 \sim C_2$ branched or straight chain alkyl optionally substituted with OH or $NR^6R^7$; $CONR^6R^7$; $CO_2R^8$; halogen; $NR^6R^7$; $NHSO_2NR^6R^7$; $NHSO_2R^9$; $SO_2NR^{10}R^{11}$; or phenyl, pyridyl, pyrimidinyl, imidazolyl, oxazolyl, thiazolyl, thienyl, or triazolyl, either of which is optionally substituted with methyl;

$R^6$ and $R^7$ are each independently H or $C_1 \sim C_4$ branched or straight chain alkyl; or $R^6$ and $R^7$ together with their attached nitrogen atom form pyrrolinyl, piperidyl, morpholinyl, 4-N($R^{12}$)-piperazinyl or imidazolyl, either of which is optionally substituted with methyl or hydroxyl;

$R^8$ is H; $C_1 \sim C_6$ branched or straight chain alkyl optionally substituted with $C_1 \sim C_4$ alkoxyl, $C_1 \sim C_4$ alkylamino, dialkylamino; substituted phenyl and substituted heterocyclic group in which the substitute(s) on the ring of substituted phenyl and substituted heterocyclic group are defined as the above;

$R^9$ is $C_1 \sim C_3$ alkyl optionally substituted with $NR^6R^7$;

$R^{10}$ and $R^{11}$ are each independently H or $C_1 \sim C_{12}$ branched or straight chain alkyl; $C_1 \sim C_3$ halogenated branched or straight chain alkyl; $C_2 \sim C_6$ alkenyl; $C_2 \sim C_6$ alkynyl or $C_3 \sim C_6$ cycloalkyl; or $R^{10}$ and $R^{11}$ take together to form a pyrrolinyl, pyrrolinone group, piperidyl, morpholinyl, 4-N($R^{13}$)-piperazinyl; or $R^{10}$ and $R^{11}$ together with their attached nitrogen atom form a pyrrolinyl, pyrrolinone group, piperidyl, morpholinyl, or 4-N($R^{13}$)-piperazinyl; the said groups are optionally substituted with OH, CN, $CO_2R^8$, $C_1$~$C_4$ branched or straight chain alkyl, $C_1$~$C_3$ alkoxyl, $NR^{14}R^{15}$ or $CONR^{14}R^{15}$; substituted phenyl, substituted heterocyclic group, or $C_1$-$C_6$ branched or straight chain alkyl substituted with substituted phenyl or substituted heterocyclic group, the said groups are optionally further substituted with OH, $CO_2R^8$, $NR^{14}R^{15}$, $CONR^{14}R^{15}$, or linked together with another substituted phenyl or substituted heterocyclic group by a carbonyl group;

$R^{12}$ is H; $C_1$~$C_6$ branched or straight chain alkyl which may be optionally substituted with phenyl, $C_2$~$C_3$ alkyl substituted by hydroxyl, or $C_1$~$C_4$ alkoxyl; $C_1$~$C_3$ fluoroalkyl; $C_2$~$C_6$ alkenyl; $C_2$~$C_6$ alkynyl; or $C_3$~$C_6$ cycloalkyl; $R^{13}$ is H; $C_1$~$C_6$ branched or straight chain alkyl; $C_2$~$C_6$ branched or straight chain alkyl substituted with $C_1$~$C_3$ alkoxyl; $C_2$~$C_6$ branched or straight chain alkyl substituted with hydroxyl; $C_2$~$C_6$ branched or straight chain alkyl substituted with $NR^{14}R^{15}$; $C_2$~$C_6$ branched or straight chain alkyl substituted with phenyl; $C_1$~$C_6$ branched or straight chain alkyl substituted with $CONR^{14}R^{15}$; $C_2$~$C_6$ branched or straight chain hydrocarbyl substituted with $CO_2R^8$; $C_2$~$C_6$ branched or straight chain hydrocarbyl having substituted phenyl or substituted heterocyclic group as substituent; $CO_2R^8$, $CONR^{14}R^{15}$, $CSNR^{14}R^{15}$ or $C(NH)NR^{14}R^{15}$; $C_1$~$C_3$ halogenated branched or straight chain alkyl; $C_2$~$C_6$ alkenyl; $C_2$~$C_6$ alkynyl or $C_3$~$C_6$ cylcloalkyl; or polyethylene glycol group (n=2~20), which is optionally substituted with $C_1$~$C_6$ alkyl on its terminal;

$R^{14}$ and $R^{15}$ are each independently H; $C_1$~$C_4$ branched or straight chain alkyl; $C_2$~$C_4$ branched or straight chain alkyl substituted with $C_1$~$C_3$ alkoxyl; or $C_2$~$C_4$ branched or straight chain alkyl substituted with hydroxyl; or $R^{14}$ and $R^{15}$ together with their attached nitrogen atom form a pyrrolinyl, pyrrolinone group, piperidyl or morpholinyl; and the substituted phenyl refers to a phenyl which is substituted with one or more groups selected from $C_1$~$C_4$ alkoxyl, halogen, cyano-, $CF_3$, $OCF_3$, $C_1$~$C_4$ branched or straight chain alkyl on the phenyl ring; The substituted heterocyclic group refers to hexatomic rings containing one or two nitrogen atoms; and the oxides thereof; pentatomic rings containing two or three hetero-atom selected a group consisted of nitrogen, oxygen, and sulfur atoms; the substituting groups on the heterocyclic ring are $C_1$~$C_4$ branched or straight chain alkyl, $C_1$~$C_4$ alkoxyl, amino, as well as $C_1$~$C_4$ branched or straight chain alkyl amino, $C_1$~$C_4$ alkoxylamino group.

In another aspect, the invention provides processes for preparation of compounds of the formula I and intermediates used in the preparation thereof.

The process for preparation of compounds of the general formula I comprises:

The compounds of formula IE with a compound of formula IF

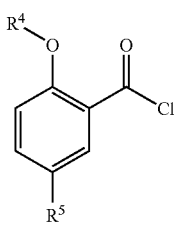

IE

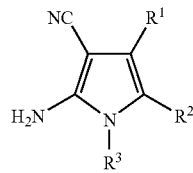

IF wherein $R^1$, $R^2$, $R^3$, $R^4$ and $R^5$ are defined as previous, are reacted in an inert solvent such as dichloromethane and toluene and the like to produce the compounds of formula ID,

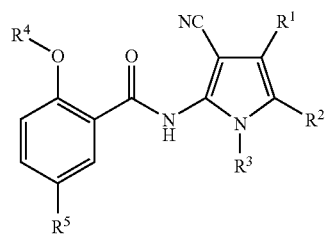

ID

Wherein $R^1$, $R^2$, $R^3$, $R^4$ and $R^5$ are defined as previous.

This reaction is carried out in the presence of an organic base such as tertiary amine, pyridine as a catalyst as well as an acid neutralizer at −20° C. to 80° C.

And then compounds of formula IA may be obtained by heating compounds of formula ID in an acidic aqueous solution, generally phosphoric acid aqueous solution:

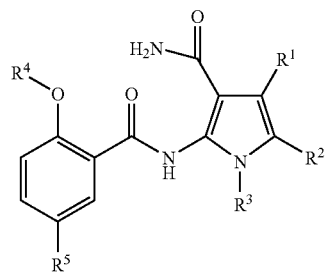

IA

Wherein $R^1$, $R^2$, $R^3$, $R^4$ and $R^5$ are as previously defined.

And then the compounds of formula I is obtained by a cyclization reaction of compounds of formula IA:

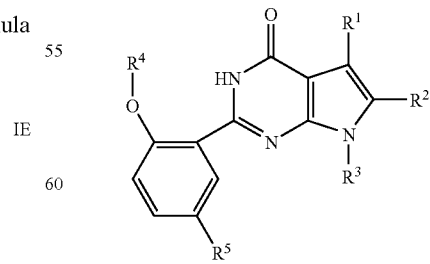

I

Wherein $R^1$, $R^2$, $R^3$, $R^4$ and $R^5$ are defined as previous.

The cyclization reaction is similar to a conventional method known for synthesis of pyrimidone. The reaction may be carried out by reflux in an appropriate solution under acidic, basic or neutral condition. Preferably using alkali metal salts of alcohol or amine, or an organic base, and ethanol as a solvent. Thus, for example, the cyclization reaction is carried out by refluxing in ethanol and in the presence of potassium tert-butoxide or sodium ethoxide.

Also, compounds of formula I may be obtained directly by cyclization reaction of corresponding compounds of the formula ID.

Generally, this reaction is carried out by heating the formula ID in a mixture of $P_2O_5$, water and tertiary amine, especially dimethylcyclohexylamine at 100° C. to 300° C.

In an alternative procedure, the reaction may be carried out at room temperature or by heating in an alkaline hydrogen peroxide water solution, for example a mixture of hydrogen peroxide and urea.

The said reaction may also be carried out at room temperature or by heating under anhydrous or hydrous acidic conditions generally using hydrochloric acid.

The specific example of compounds of formula I wherein $R^5$ is $SO_2NR^{11}R^{12}$ may be prepared by following process.

Compounds of formula IC can be readily prepared from compounds of the formula IF and the IE wherein $R^5$ is H,

IC wherein $R^1$, $R^2$, $R^3$ and $R^4$ are defined as previous.

And then compounds of the formula IB are prepared by the reaction of compounds of the formula IC with chlorosulfonic acid:

IB wherein $R^1$, $R^2$, $R^3$ and $R^4$ are defined as previous.

The reaction is generally carried out by heating the formula IC in the presence of an excess amount of chlorosulfonic acid. Also, the said reaction may be performed in solvent of dichloromethane, chloroform, and other inert or polar non-proton solvents. In particular when the reactant has a poor solubility in chlorosulfonic acid, using above-mentioned solvents seem to be more important. The reaction can be carried out at the temperature as high as 100° C. without producing any by-products, but generally in ice bath.

Acylation reaction is carried out by reacting the compounds of the formula IB with proper amines to obtain the compounds of formula I wherein $R^5$ is $SO_2NR^{11}R^{12}$, and $R^{11}$, $R^{12}$ are defined as previous.

The said acylation reaction may be performed in the solvents of dichloromethane, chloroform, tertiary amine and other inert or polar non-proton solvents at −78° C. to 100° C. using equal or excess amounts of amines. The excess amount of amine is used not only as a reactant, but also a solvent.

Either, compounds of the formula I are prepared by reacting formula IG with compounds of formula IH, compound IG is compound I wherein $R^3$ is H:

IG wherein $R^1$, $R^2$, $R^4$ and $R^5$ are defined as previous.

$R^3$—X    IH wherein X represents Cl, Br or I; $R^3$ is defined as previous.

The said reactions are carried out by heating reflux in the solvents of non-polar proton solvents with organic or non-organic base as catalyst, generally alkali carbonate such as potassium carbonate in ketone solvents such as acetone.

Optionally, compounds of the formula I can be converted into the corresponding salts by reacting with pharmaceutically acceptable acids.

The intermediates of formula IE are prepared from corresponding aromatic carboxylic acid that is commercially available and thionyl chloride, oxalyl chloride by conventional synthesis method of acyl chloride.

If using oxalyl chloride, the reaction should be carried out in the non-proton solvents such as dichloromethane, chloroform, toluene etc. at the temperature of −10° C. to 60° C. for 2-10 hours using an equal or excess (no more than 4 fold) amount of oxalyl chloride in the presence of 0.05-1 equivalent of dimethylformamide as a catalyst. The said reaction solutions may be directly used in the preparation of the formula ID or distilled under the reduced pressure to prepare the purified compounds.

If using thionyl chloride, the reaction should be performed in the non-proton solvents such as dichloromethane, chloroform, toluene etc., or the thionyl chloride itself is used as solvent, and better, under the conditions of reflux for 0.5-3 hours. The obtained solutions may be directly used in the preparation of the formula ID, or distilled under the reduced pressure to prepare the purified compounds.

Intermediates of the formula IF used may be synthesized readily from malononitrile and correspondingly substituted 2-aminoketones by conventional synthetic procedures in accordance with literatures described below:

Wiley R. H., et al, J Am. Chem. Soc, 1948. 70, 2005; Johnson R. W. et al, J Heterocyclic Chem. 1997, 14, 383; and Wamhoff H. et al, Synthesis 1976, 51.

The reaction may be carried out in water in the presence of alkali metal hydroxide such as potassium hydroxide or sodium hydroxide etc. as the catalyst at the temperature of 4° C. to 60° C. The reaction solution is diluted and filtrated, and dried to obtain the product. If the low water-soluble substituted 2-aminoketones is used, the reaction may be carried out either in two phases of both water and organic reagents in the presence of phase transfer catalysts, or in organic solvents in the presence of nitrogenous organic base such as pyridine, triethylamine as catalyst. The resulting compounds can be purified by recrystallization.

Another aspect of the invention relates to a pharmaceutical composition for treatment of erectile dysfunction in a male animal, including man, comprising a compound of formula I or a pharmaceutically acceptable salt thereof, together with one or more pharmaceutically acceptable diluent, excipient or carrier.

Another aspect of this invention relates to a process for the preparation of a pharmaceutical composition for treatment or prevention of erectile dysfunction in a male animal, including man, comprising formulating a compound of formula I or a pharmaceutically acceptable salt thereof with pharmaceutically acceptable diluent, excipient or carrier.

Although the compounds of the invention are envisaged primarily for the treatment of erectile dysfunction or male sexual dysfunction, they may also be useful for the treatment of female sexual dysfunction including orgasmic dysfunction related to clitoral disturbances.

Thus, the aspect of this invention provides the use of a compound of formula I for curing or preventing erectile dysfunction in a male animal, including man, and PDE5-related diseases.

The aforementioned PDE5-related diseases include male sexual (erectile) dysfunction, female sexual dysfunction, premature delivery, dysmenorrhea, benign prostatic hyperlasia, bladder obstruction, incontinence, stable or unstable angina, hypertension, pulmonary hypertension, congestive heart failure, atherosclerosis, stroke, peripheral circulatory disease, low vascular patency, chronic asthma, allergic asthma, bronchitis, allergic rhinitis, glaucoma, disorder of the gastrointestinal movement, forerunner of the seizure, Kawasaki disease, tolerance of nitric acid ester, multiple sclerosis, peripheral nerve syndrome caused by diabetes, Alzheimer disease (AD), acute respiratory system failure, psoriasis, cutaneous gangrene, metastasis of cancer cell, loss of hair, nutcracker oesophagus, anal fissure, and hypoxia-induced vasoconstriction.

The compounds of the invention can exist in tautomeric forms. It is to be understood that all tautomers and other isomers of formula I as well as the mixture thereof fall into the claimed scope of this invention.

The compounds of this invention may contain one or more asymmetric centers and thus can exist as epimers or optical isomers. Furthermore, they are separated into enantiomers by the conventional methods such as dynamic crystallization or chromatography. Besides, they are synthesized from chiral starting materials or reagents by way of asymmetric synthesis. It is to be understood that all epimers or optical as well as the mixture thereof fall into the claimed scope of this invention.

The compounds of this invention may form pharmaceutically acceptable salts with organic or inorganic acid as well as organic or inorganic alkali.

It is to be understood that this invention includes both mixtures and separate individual pharmaceutically acceptable salts formed by reacting the compounds of this invention with organic or inorganic alkali as well as organic or inorganic acid such as hydrochloric acid, hydrobromic acid, sulfuric acid, phosphoric acid, acetic acid, citric acid, tartaric acid, gluconic acid, lactic acid, maleic acid, fumaric acid, methane-sulfonic acid, hydroxyacetic acid, succinic acid, 4-toluene sulfonic acid, galacturonic acid, glutamic acid, aspartic acid, and the like.

Preferred compounds of this invention refer to the following compounds of formula I as well as the pharmaceutically acceptable salts thereof:

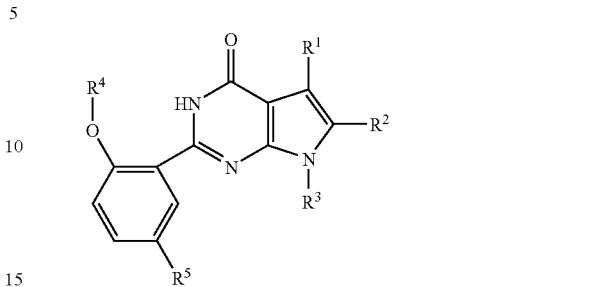

wherein:

$R^1$ is $C_1\sim C_3$ branched or straight chain alkyl optionally substituted with one or more groups selected from a group consisted of the following: $C_1\sim C_4$ alkyl, $C_1\sim C_4$ alkoxyl, $C_1\sim C_4$ alkanoyl, substituted phenyl, substituted heterocyclic group, $CONR^6R^7$ and $NR^6R^7$;

$R^2$ is H; $C_1\sim C_3$ branched or straight chain alkyl optionally substituted with one or more groups selected from a group consisted of the following: substituted phenyl, substituted heterocyclic group, $CONR^6R^7$, and $NR^6R^7$;

$R^3$ is H; $C_2\sim C_4$ branched or straight chain alkyl which may be optionally substituted with $C_3\sim C_4$ cycloalkyl, $C_1\sim C_3$ alkoxyl; $C_2\sim C_4$ alkenyl; or $C_2\sim C_4$ alkynyl;

$R^4$ is H; $C_1\sim C_4$ branched or straight chain alkyl which may be optionally substituted with $C_3\sim C_5$ cycloalkyl or $C_1\sim C_3$ alkoxyl; $C_2\sim C_4$ alkenyl; or $C_2\sim C_4$ alkynyl;

$R^5$ is H; $C_1\sim C_4$ branched or straight chain alkyl which may be optionally substituted with OH, $NR^6R^7$, CN, $CONR^6R^7$ or $CO_2R^8$; $C_2\sim C_4$ alkoxyl optionally substituted with $NR^6R^7$; $NR^6R^7$; $NHSO_2NR^6R^7$; $NHSO_2R^9$; $SO_2NR^{10}R^{11}$; or phenyl, pyridyl, pyrimidinyl, imidazolyl, oxazolyl, thiazolyl, thienyl or triazolyl, either of which is optionally substituted with methyl;

$R^6$ and $R^7$ are each independently H; $C_1\sim C_4$ branched or straight chain alkyl, or $R^6$ and $R^7$ together with their attached nitrogen atom form a pyrrolinyl, piperidyl, morpholinyl, 4-N($R^{12}$)-piperazinyl or imidazolyl, either of which is optionally substituted with methyl and hydroxyl;

$R^8$ is H or $C_1\sim C_4$ branched or straight chain alkyl;

$R^9$ is $C_1\sim C_3$ alkyl optionally substituted with $NR^6R^7$;

$R^{10}$ and $R^{11}$ are each independently H or $C_1\sim C_{12}$ branched or straight chain alkyl; $C_1\sim C_3$ halogenated branched or straight chain alkyl; $C_2\sim C_6$ alkenyl; $C_2\sim C_6$ alkynyl or $C_3\sim C_6$ cylcoalkyl; or $R^{10}$ and $R^{11}$ take together to form a pyrrolinyl, pyrrolinone group, piperidyl, morpholinyl, 4-N($R^{13}$)-piperazinyl; or $R^{10}$ and $R^{11}$ together with their attached nitrogen atom form a pyrrolinyl, pyrrolinone group, piperidyl, morpholinyl, or 4-N($R^{13}$)-piperazinyl; the said groups the said groups are optionally substituted with OH, CN, $CO_2R^8$, $C_1\sim C_4$ branched or straight chain alkyl, $C_1\sim C_3$ alkoxyl, $NR^{14}R^{15}$, or $CONR^{14}R^{15}$; substituted phenyl, substituted heterocyclic group, or $C_1\sim C_6$ branched or straight alkyl substituted with substituted phenyl or substituted heterocyclic group, the said groups are further substituted with OH, $CO_2R^8$, $NR^{14}R^{15}$, $CONR^{14}R^{15}$, or linked together with another substituted phenyl or substituted heterocyclic group by a carbonyl group;

$R^{12}$ is H; $C_1\sim C_6$ branched or straight chain alkyl which may be optionally substituted with $C_2\sim C_3$ alkyl or $C_1\sim C_4$ alkoxyl, the said alkyl and alkoxyl are substituted with phenyl, hydroxyl; $C_2$~$C_6$ alkenyl or $C_3$~$C_6$ cylcoalkyl;

$R^{13}$ is H; $C_1$~$C_6$ branched or straight chain alkyl; $C_2$~$C_6$ branched or straight chain alkyl substituted with $C_1$~$C_3$ alkoxyl; $C_2$~$C_6$ branched or straight chain alkyl substituted with hydroxyl; $C_2$~$C_6$ branched or straight chain alkyl substituted with $NR^{14}R^{15}$; $C_2$~$C_3$ branched or straight chain alkyl substituted with phenyl; $C_1$~$C_6$ branched or straight chain alkyl substituted with $CONR^{14}R^{15}$; $CO_2R^8$, $CONR^{14}R^{15}$, $CSNR^{14}R^{15}$ or $C(NH)NR^{14}R^{15}$; $C_1$~$C_3$ halogenated branched or straight chain alkyl; $C_2$~$C_6$ alkenyl; $C_2$~$C_6$ alkynyl or $C_3$~$C_6$ cylcoalkyl;

$R^{14}$ and $R^{15}$ are each independently H; $C_1$~$C_4$ branched or straight chain alkyl; $C_2$~$C_4$ branched or straight chain alkyl substituted with $C_1$~$C_3$ alkoxyl; or $C_2$~$C_4$ branched or straight chain alkyl substituted with hydroxyl; or $R^{14}$ and $R^{15}$ together with their attached nitrogen atom form pyrrolinyl, pyrrolinone group, piperidyl, or morpholinyl;

The substituted phenyl refers to a phenyl group which is substituted with one or more groups selected from $C_1$~$C_4$ alkoxyl, halogen, CN, $CF_3$, $OCF_3$, or $C_1$~$C_4$ branched or straight chain alkyl; the substituted heterocyclic group refers to hexatomic rings containing one or two nitrogen atoms, and the oxide thereof; or pentatomic rings containing two or three hetero-atom selected a group consisted of nitrogen, oxygen and sulfur atoms; the substituents on the heterocyclic ring are $C_1$~$C_4$ branched or straight chain alkyl, $C_1$~$C_4$ alkoxyl, amino, as well as $C_1$~$C_4$ branched or straight chain alkyl amino, $C_1$~$C_4$ alkoxylamino.

In the more preferred embodiment, compounds of the general formula I and their pharmaceutically acceptable salts as follows:

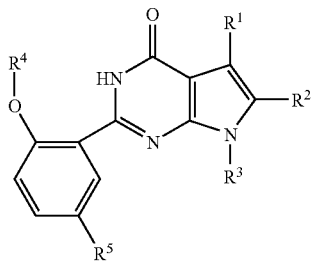

I wherein $R^1$ is $C_2$~$C_3$ branched or straight chain alkyl which may be optionally substituted with one or more groups selected from substituted heterocyclic group and $NR^6R^7$;
$R^2$ is H;
$R^3$ is H; $C_2$~$C_4$ branched or straight chain alkyl which may be optionally substituted with $C_3$~$C_4$ cycloalkyl; $C_2$~$C_4$ alkenyl; $C_2$~$C_4$ alkynyl;
$R^4$ is $C_2$~$C_4$ branched or straight chain alkyl, which may be optionally substituted with $C_1$~$C_3$ alkoxyl; $C_2$-$C_4$ alkenyl; $C_2$-$C_4$ alkynyl;
$R^5$ is $SO_2NR^{10}R^{11}$;
$R^6$ and $R^7$ together with their attached nitrogen atom form a pyrrolinyl, piperidyl or morpholinyl;
$R^8$ is H or $C_1$~$C_4$ branched or straight chain alkyl;
$R^{10}$ and $R^{11}$ are each independently H or $C_1$~$C_{12}$ branched or straight chain alkyl; $C_3$~$C_6$ cylcoalkyl; or $R^{10}$ and $R^{11}$ take together to form a pyrrolinyl, pyrrolinone group, piperidyl, morpholinyl, 4-N($R^{13}$)-piperazinyl; or $R^{10}$ and $R^{11}$ together with their attached nitrogen atom form a pyrrolinyl, pyrrolinone group, piperidyl, morpholinyl, or 4-N($R^{13}$)-piperazinyl; the said groups are optionally substituted with OH, $C_1$~$C_4$ branched or straight chain alkyl, $C_1$~$C_3$ alkoxyl, $NR^{14}R^{15}$, or $CONR^{14}R^{15}$; substituted phenyl, substituted heterocyclic group, or $C_1$~$C_6$ branched or straight alkyl optionally substituted with substituted phenyl, substituted heterocyclic group, the said groups are further substituted with OH, $CO_2R^8$, $NR^{14}R^{15}$ or $CONR^{13}R^{14}$, or linked together with another substituted phenyl or substituted heterocyclic group by a carbonyl;

$R^{13}$ is H; $C_1$~$C_3$ branched or straight chain alkyl; $C_2$~$C_3$ branched or straight chain alkyl substituted with $C_1$~$C_3$ alkoxyl; $C_2$~$C_3$ branched or straight chain alkyl substituted with OH; $C_2$~$C_6$ branched or straight chain alkyl substituted with $NR^{14}R^{15}$; $C_2$~$C_3$ branched or straight chain alkyl substituted with phenyl; $C_1$~$C_6$ branched or straight chain alkyl substituted with $CONR^{14}R^{15}$; $CO_2R^8$ or $CONR^{14}R^{15}$;

$R^{14}$ and $R^{15}$ are each independently H; $C_1$~$C_4$ branched or straight chain alkyl; $C_2$~$C_4$ branched or straight chain alkyl substituted with $C_1$~$C_3$ alkoxyl; or $C_2$~$C_4$ branched or straight chain alkyl substituted with OH; or $R^{14}$ and $R^{15}$ together with their attached nitrogen atom form a pyrrolinyl, pyrrolinone group, piperidyl or morpholinyl;

the substituted phenyl refers to a phenyl group which is substituted with one or more substituents selected from a group consisted of $C_1$~$C_4$ alkoxyl, halogen, CN, $CF_3$, $OCF_3$, and $C_1$~$C_4$ branched or straight chain alkyl; the substituted heterocyclic group refers to hexatomic rings containing one or two nitrogen atoms and the oxide thereof; or pentatomic rings containing two or three hetero-atom selected a group consisted of nitrogen, oxygen, and sulfur atoms; the substituents on the heterocyclic ring are $C_1$~$C_4$ branched or straight chain alkyl, $C_1$~$C_4$ alkoxyl, amino, as well as $C_1$~$C_4$ branched or straight chain alkyl amino, $C_1$~$C_4$ alkoxylamino.

Especially preferred compounds of invention include:
2-[2-ethoxyl-5-(4-ethylpiperazinyl-1-sulfonyl)phenyl]-5-methyl-7-n-propyl-3,7-dihydropyrrolo[2,3-d]pyrimidin-4-one, the monohydrochloride, dihydrochloride and other possible hydrochloride thereof;
2-[2-methoxyl-5-(4-ethylpiperazinyl-1-sulfonyl)phenyl]-5-methyl-7-n-propyl-3,7-dihydropyrrolo[2,3-d]pyrimidin-4-one, the monohydrochloride, dihydrochloride and other possible hydrochloride thereof;
2-[2-n-propoxy-5-(4-ethylpiperazinyl-1-sulfonyl)phenyl]-5-methyl-7-n-propyl-3,7-dihydropyrrolo[2,3-d]pyrimidin-4-one, the monohydrochloride, dihydrochloride and other possible hydrochloride thereof;
2-[2-allyloxy-5-(4-ethylpiperazinyl-1-sulfonyl)phenyl]-5-methyl-7-n-propyl-3,7-dihydropyrrolo[2,3-d]pyrimidin-4-one, and the monohydrochloride, dihydrochloride and other possible hydrochloride thereof;
2-[2-n-propoxy-5-(4-ethylpiperazinyl-1-sulfonyl)phenyl]-5-ethyl-7-n-propyl-3,7-dihydropyrrolo[2,3-d]pyrimidin-4-one, the monohydrochloride, dihydrochloride and other possible hydrochloride thereof;
2-[2-ethoxyl-5-(4-methylpiperazinyl-1-sulfonyl)phenyl]-5-methyl-7-n-propyl-3,7-dihydropyrrolo[2,3-d]pyrimidin-4-one, the monohydrochloride, dihydrochloride and other possible hydrochloride thereof;
2-[2-ethoxyl-5-(4-methylpiperazinyl-1-sulfonyl)phenyl]-5-ethyl-7-n-propyl-3,7-dihydropyrrolo[2,3-d]pyrimidin-4-one, the monohydrochloride, dihydrochloride and other possible hydrochloride thereof;
2-[2-ethoxyl-5-(4-ethoxycarbonylpiperazinyl-1-sulfonyl) phenyl]-5-methyl-7-n-propyl-3,7-dihydropyrrolo[2,3-d] pyrimidin-4-one, the monohydrochloride, dihydrochloride and other possible hydrochloride thereof;
2-[2-ethoxyl-5-(4-(2-hydroxyethyl)piperazinyl-1-sulfonyl) phenyl]-5-methyl-7-n-propyl-3,7-dihydropyrrolo[2,3-d]

pyrimidin-4-one, the monohydrochloride, dihydrochloride and other possible hydrochloride thereof;

2-[2-ethoxyl-5-(pyrrolidinyl-1-sulfonyl)phenyl]-5-methyl-7-n-propyl-3,7-dihydropyrrolo[2,3-d]pyrimidin-4-one, the monohydrochloride, dihydrochloride and other possible hydrochloride thereof;

2-{2-ethoxyl-5-[3-(2-oxy-pyrrolidin-1-yl)-n-propylamino-N-sulfonyl]phenyl}-5-methyl-7-n-propyl-3,7-dihydropyrrolo[2,3-d]pyrimidin-4-one, the monohydrochloride, dihydrochloride and other possible hydrochloride thereof;

2-{2-ethoxyl-5-[2-(pyrrolidin-1-yl)-ethylamino-N-sulfonyl]phenyl}-5-methyl-7-n-propyl-3,7-dihydropyrrolo[2,3-d]pyrimidin-4-one, the monohydrochloride, dihydrochloride and other possible hydrochloride thereof;

2-[2-ethoxyl-5-(morpholino-4-sulfonyl)phenyl]-5-methyl-7-n-propyl-3,7-dihydropyrrolo[2,3-d]pyrimidin-4-one, the monohydrochloride, dihydrochloride and other possible hydrochloride thereof;

2-[2-ethoxyl-5-(3-(morpholin-4-yl)-n-propylamino-N-sulfonyl)phenyl]-5-methyl-7-n-propyl-3,7-dihydropyrrolo[2,3-d]pyrimidin-4-one, the monohydrochloride, dihydrochloride and other possible hydrochloride thereof;

2-[2-ethoxyl-5-(2-(morpholin-4-yl)-ethylamino-N-sulfonyl)phenyl]-5-methyl-7-n-propyl-3,7-dihydropyrrolo[2,3-d]pyrimidin-4-one, the monohydrochloride, dihydrochloride and other possible hydrochloride thereof;

2-[2-ethoxyl-5-(2,6-dimethylmorpholino-N-sulfonyl)phenyl]-5-methyl-7-n-propyl-3,7-dihydropyrrolo[2,3-d]pyrimidin-4-one, the monohydrochloride, dihydrochloride and other possible hydrochloride thereof;

2-[2-ethoxyl-5-(1-benzylpiperidyl-4-aminosulfonyl)phenyl]-5-methyl-7-n-propyl-3,7-dihydropyrrolo[2,3-d]pyrimidin-4-one, the monohydrochloride, dihydrochloride and other possible hydrochloride thereof;

2-[2-ethoxyl-5-(2-(piperidin-1-yl)ethylamino-1-sulfonyl)phenyl]-5-methyl-7-n-propyl-3,7-dihydropyrrolo[2,3-d]pyrimidin-4-one, the monohydrochloride, dihydrochloride and other possible hydrochloride thereof;

2-[2-ethoxyl-5-(4-benzylpiperazinyl-1-sulfonyl)phenyl]-5-methyl-7-n-propyl-3,7-dihydropyrrolo[2,3-d]pyrimidin-4-one, the monohydrochloride, dihydrochloride and other possible hydrochloride thereof;

2-[2-ethoxyl-5-(4-phenylpiperazinyl-1-sulfonyl)phenyl]-5-methyl-7-n-propyl-3,7-dihydropyrrolo[2,3-d]pyrimidin-4-one, the monohydrochloride, dihydrochloride and other possible hydrochloride thereof;

2-[2-ethoxyl-5-(piperazinyl-1-sulfonyl)phenyl]-5-methyl-7-n-propyl-3,7-dihydropyrrolo[2,3-d]pyrimidin-4-one, the monohydrochloride, dihydrochloride and other possible hydrochloride thereof;

2-[2-ethoxyl-5-(4-benzo[1,3]dioxol-5-yl-methylpiperazinyl-1-sulfonyl)phenyl]-5-methyl-7-n-propyl-3,7-dihydropyrrolo[2,3-d]pyrimidin-4-one, the monohydrochloride, dihydrochloride and other possible hydrochloride thereof;

2-{2-ethoxyl-5-[4-(3-phenyl-n-propan-1-yl)piperidyl-1-sulfonyl]phenyl-5-methyl-7-n-propyl-3,7-dihydropyrrolo[2,3-d]pyrimidin-4-one, the monohydrochloride, dihydrochloride and other possible hydrochloride thereof;

2-[2-ethoxyl-5-(n-propylamino-1-sulfonyl)phenyl]-5-methyl-7-n-propyl-3,7-dihydropyrrolo[2,3-d]pyrimidin-4-one, the monohydrochloride, dihydrochloride and other possible hydrochloride thereof;

2-[2-ethoxyl-5-(N,N-di(2-hydroxyethyl)aminosulfonyl)phenyl]-5-methyl-7-n-propyl-3,7-dihydropyrrolo[2,3-d]pyrimidin-4-one, the monohydrochloride, dihydrochloride and other possible hydrochloride thereof;

2-{2-ethoxyl-5-[N-(2-hydroxyethyl)-N-methyl]aminosulfonyl}phenyl}-5-methyl-7-n-propyl-3,7-dihydropyrrolo[2,3-d]pyrimidin-4-one, the monohydrochloride, dihydrochloride and other possible hydrochloride thereof;

2-{2-ethoxyl-5-[N-(2-hydroxyethyl)-N-ethyl]aminosulfonyl}phenyl}-5-methyl-7-n-propyl-3,7-dihydropyrrolo[2,3-d]pyrimidin-4-one, the monohydrochloride, dihydrochloride and other possible hydrochloride thereof;

2-{2-ethoxyl-5-[N-(2-hydroxyethyl)-N-n-butyl]aminosulfonyl}phenyl}-5-methyl-7-n-propyl-3,7-dihydropyrrolo[2,3-d]pyrimidin-4-one, the monohydrochloride, dihydrochloride and other possible hydrochloride thereof;

2-{2-ethoxyl-5-(p-ethoxylcarboxylphenylamino)-N-sulfonyl}phenyl}-5-methyl-7-n-propyl-3,7-dihydropyrrolo[2,3-d]pyrimidin-4-one, the monohydrochloride, dihydrochloride and other possible hydrochloride thereof;

2-{2-ethoxyl-5-(o-benzoylphenylamino)-N-sulfonyl}phenyl}-5-methyl-7-n-propyl-3,7-dihydropyrrolo[2,3-d]pyrimidin-4-one, the monohydrochloride, dihydrochloride and other possible hydrochloride thereof;

2-{2-ethoxyl-5-(N2-acethydrazido)-N1-sulfonyl}phenyl}-5-methyl-7-n-propyl-3,7-dihydropyrrolo[2,3-d]pyrimidin-4-one, the monohydrochloride and dihydrochloride and other possible hydrochloride thereof;

2-{2-ethoxyl-5-(2-dimethylaminoethylamino)-N-sulfonyl}phenyl}-5-methyl-7-n-propyl-3,7-dihydropyrrolo[2,3-d]pyrimidin-4-one, the monohydrochloride, dihydrochloride and other possible hydrochloride thereof;

2-[2-ethoxyl-5-(4-ethylpiperazinyl-1-sulfonyl)phenyl]-5-ethyl-7-n-propyl-3,7-dihydropyrrolo[2,3-d]pyrimidin-4-one, the monohydrochloride, dihydrochloride and other possible hydrochloride thereof;

2-[2-ethoxyl-5-(4-ethylpiperazinyl-1-sulfonyl)phenyl]-5-morpholinomethyl-7-n-propyl-3,7-dihydropyrrolo[2,3-d]pyrimidin-4-one, the monohydrochloride, dihydrochloride and other possible hydrochloride thereof;

2-[2-ethoxyl-5-(4-ethylpiperazinyl-1-sulfonyl)phenyl]-5-(pyrimidinyl-2)-methyl-7-n-propyl-3,7-dihydropyrrolo[2,3-d]pyrimidin-4-one, the monohydrochloride, dihydrochloride and other possible hydrochloride thereof;

and 2-[2-ethoxyl-5-(4-ethylpiperazinyl-1-sulfonyl)phenyl]-5-methyl-7-allyl-3,7-dihydropyrrolo[2,3-d]pyrimidin-4-one, the monohydrochloride, dihydrochloride and other possible hydrochloride thereof.

The compounds of general formula I can not only be prepared into orally-administrated solid formulations, such as the tablets, pills, capsules and powder, but also liquid ones, such as suspensions, solution, emulsion and syrup. All of these formulations may comprise a variety of conventional excipients, such as the wetting agents, sweet-enhancers, aromatics and preservatives, etc., they may also comprise some other conventional functional excipients, such as the fillers (starch and carbohydrates), binders (carboxymethylcellulose etc.), dispersants (calcium carbonate and sodium carbonate etc.), diluents (glycerol), absorption enhancers (quaternary ammonium compounds), lubricants (stearate) and absorption agents (kaolin).

The compounds of the formula I can be prepared into ointment for external use. Likewise, they can be also prepared into intravenous injections.

Generally, for human, oral administration of the compounds of this invention is the preferred route, being the most convenient route and avoiding the disadvantages associated with administration in corpus cavernosum. In circumstances where the patients suffers from a swallowing disorder or from impairment of drug absorption after oral administration, the drug may be administered parenterally, e.g. sublingually, buccally, transdermally or injection.

For veterinary use, a compound of formula I or a non-toxic salt thereof is administered as a suitable acceptable formulation in accordance with common veterinary practice and the veterinary surgeon will determine the dose range and route of administration, which will be the most appropriate for a particular male animal.

Furthermore, none of any obvious sign of adverse acute toxicity is shown for the compounds of this invention tested in rat and dog, both intravenously (i.v.) and orally (p.o.) at up to 3 mg/Kg, has shown. For the situation of mice, no deaths occurred after doses of up to 100 mg/Kg i.v. The $LD_{50}$ for a single dose of compound I-HCl in mice is 2000 mg/kg.

BEST MODES FOR CARRYING OUT THE INVENTION

Now, the preparing methods of the compounds of the present invention are further illustrated by the preparation of 2-[2-ethoxyl-5-(4-ethylpiperazinyl-1-sulfonyl)phenyl]-5-methyl-7-n-propyl-3,7-dihydropyrrolo[2,3-d]pyrimidin-4-one, the monohydrochloride and dihydrochloride thereof as example.

Example 1

Preparation of 2-[2-ethoxyl-5-(4-ethylpiperazinyl-1-sulfonyl)phenyl]-5-methyl-7-n-propyl-3,7-dihydro-pyrrolo[2,3-d]pyrimidin-4-one, its monohydrochloride and dihydrochloride Route of Synthesis

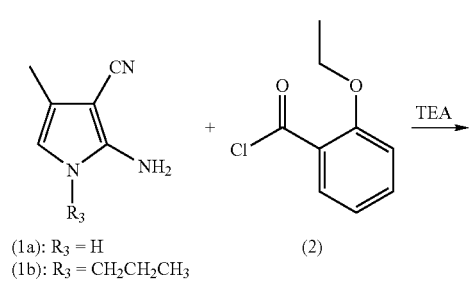

(1a): $R_3$ = H
(1b): $R_3$ = $CH_2CH_2CH_3$

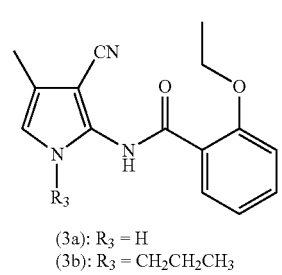

(3a): $R_3$ = H
(3b): $R_3$ = $CH_2CH_2CH_3$

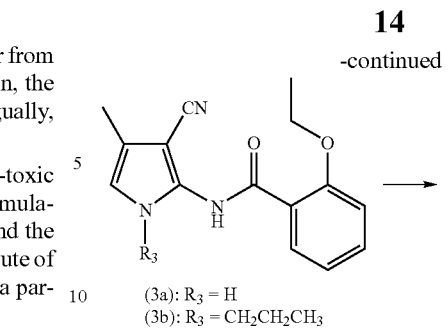

(3a): $R_3$ = H
(3b): $R_3$ = $CH_2CH_2CH_3$

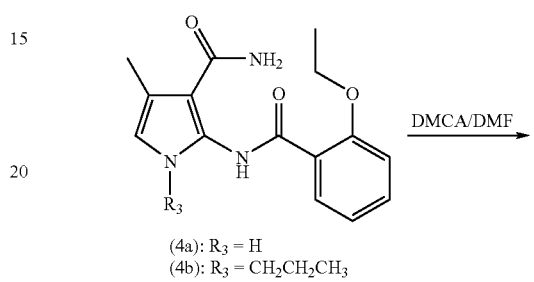

(4a): $R_3$ = H
(4b): $R_3$ = $CH_2CH_2CH_3$

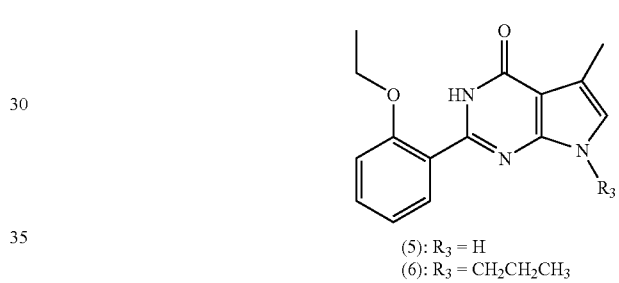

(5): $R_3$ = H
(6): $R_3$ = $CH_2CH_2CH_3$

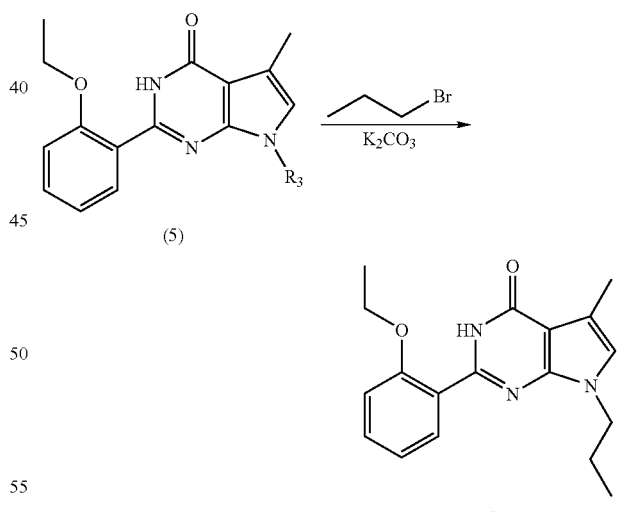

(5)

(6)

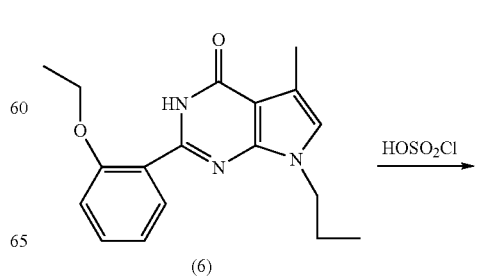

(6)

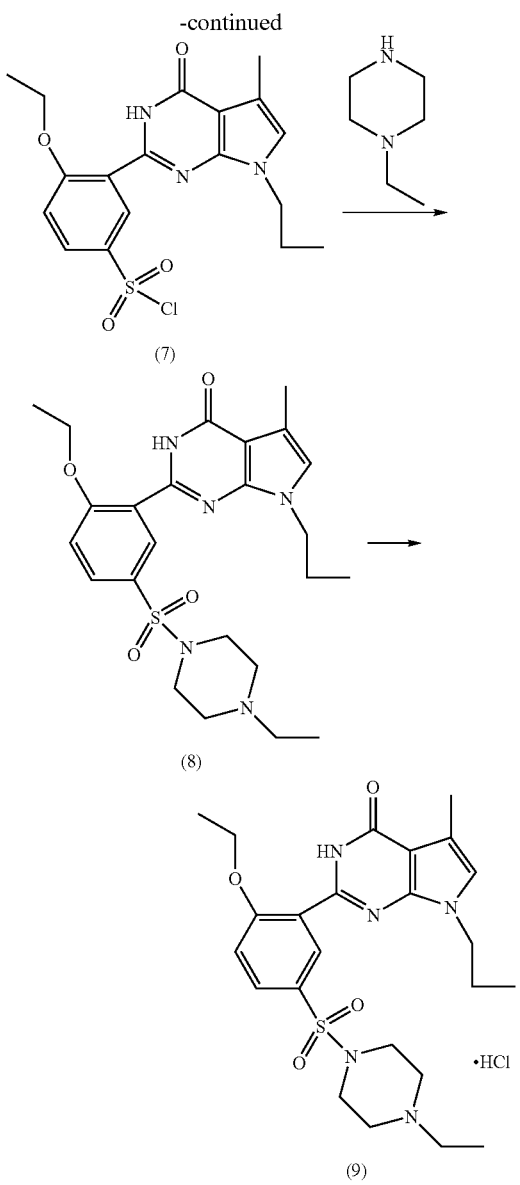

(1a) 2-amino-3-cyano-4-methylpyrrole;
(1b) N-propyl-2-amino-3-cyano-4-methylpyrrole;
(2) 2-ethoxylbenzoyl chloride;
(3a) N-(3-cyano-4-methyl-1H-pyrrol-2-yl)-2-ethoxylbenzamide;
(3b) N-(3-cyano-4-methyl-1-n-propyl-1H-pyrrol-2-yl)-2-ethoxylbenzamide;
(4a) 2-(2-ethoxylbenzamido)-4-methyl-1H-pyrrolo-3-formamide;
(4b) 2-(2-ethoxylbenzamido)-4-methyl-1-n-propyl-1H-pyrrolo-3-formamide;
(5) 2-(2-ethoxyphenyl)-5-methyl-3,7-dihydro-pyrrolo[2,3-d]pyrimidin-4-one;
(6) 2-(2-ethoxyphenyl)-5-methyl-7-n-propyl-3,7-dihydropyrrolo[2,3-d]pyrimidin-4-one;
(7) 4-ethoxyl-3-(5-methyl-4-oxy-7-n-propyl-3,7-dihydropyrrolo[2,3-d]pyrimidin-2-yl)benzenesulfonyl chloride;
(8) 2-[2-ethoxyl-5-(4-ethylpiperazinyl-1-sulfonyl)phenyl]-5-methyl-7-n-propyl-3,7-dihydropyrrolo[2,3-d]pyrimidin-4-one.

Preparation 1

N-(3-cyano-4-methyl-1H-pyrrol-2-yl)-2-ethoxylbenzamide (3a) and N-(3-cyano-4-methyl-1-n-propyl-1H-pyrrol-2-yl)-2-ethoxylbenzamide (3b)

2-ethoxyl benzoic acid (10.0 g, 60.2 mmol) was added into thionyl chloride (20 ml), and the mixture and was refluxed with agitation for 40 minutes, and the excess amount of thionyl chloride was evaporated under reduced pressure. The residual was dissolved into dichloromethane (150 ml).

Within 30 minutes and being stirred on ice bath, the afore-obtained solution of 2-ethoxyl benzoyl chloride was dropped into the compound (1a) (7.0 g, 56.8 mmol) dissolved in tetrahydrofuran (80 ml) and triethylamine (8.5 ml, 61.0 mmol). After completion, the mixture was stirred for 1 hour at 0□. After being washed with water and filtrated with diatomaceous earth, the reaction solution was mixed with 20 g of silica gel and evaporated to dryness. The resulting residual was eluted with dichloromethane by using silica gel (80 g) column to obtain 7.5 g of solid product (3a) with the yield of 48%. Furthermore, the sample for analysis was prepared by column chromatography (developing agent: dichloromethane:n-hexane=1:2) and recrystallization (dichloromethane:n-hexane=1:5).

mp 183~184° C. (sublimation 162° C.)

IR (cm$^{-1}$): 3326, 3309, 2981, 2938, 2915, 2854, 2208, 1647, 1593, 1471, 1309, 1302, 1232, 1039, 923, 727, 655, 648;

$^1$H NMR (CDCl$_3$): δ1.70 (t, J=7.0 Hz, 3H), 2.15 (s, 3H), 4.32 (q, J=7.0 Hz, 2H), 6.24 (s, 1H), 7.04 (d, 1H), 7.10 (m, 1H), 7.51 (dd, 1H), 8.20 (dd, J=7.9 and 1.8 Hz, 1H), 10.69 (brs, 1H), 10.80 (s, 1H);

$^{13}$C NMR (CDCl$_3$): δ (CH3) 10.6, 15.0; (CH2) 65.7; (CH) 110.3, 112.3, 121.4 132.1, 134.2; (C) 78.7, 115.6, 119.2, 119.4, 136.7, 157.0, 163.2;

MS (ES$^+$): m/z 287 (M+NH$_4$).

Elemental analysis (C$_{15}$H$_{15}$N$_3$O$_2$): C 66.90%; H 5.61%; N 15.60%; O 11.88%.

The compound (3b) was prepared from compound (1b) according to the above-mentioned method with the yield of 41%.

mp 58~61° C.;

IR (cm$^{-1}$): 3596, 3336, 2969, 2937, 2877, 2216, 1676, 1658, 1603, 1571, 1537, 1475, 1431, 1292, 1232, 1122, 1037, 927, 789, 752, 577;

$^1$H NMR (CDCl$_3$): δ 0.88 (t, J=7.4 Hz, 3H), 1.58 (t, J=7.0 Hz, 3H), 1.75 (m, 2H), 2.16 (s, 3H), 3.73 (t, J=7.4 Hz, 2H), 4.30 (q, J=7.0 Hz, 2H), 6.36 (s, 1H), 7.04 (d, 1H), 7.11 (m, 1H), 7.48 (dd, 1H), 8.23 (dd, J=7.9 and 1.8 Hz, 1H), 9.62 (brs, 1H);

$^{13}$C NMR (CDCl$_3$): δ (CH3) 11.1, 14.8; (CH2) 23.6, 48.3, 65.2; (CH) 112.5, 117.0, 121.3, 132.5, 134.1; (C) 89.2, 115.6, 119.8, 120.5, 131.2, 157.1, 165.0;

MS (ES$^+$): m/z 329 (M+NH$_4$).

Preparation 2

2-(2-ethoxylbenzamido)-4-methyl-1H-pyrrolo-3-formamide (4a) and 2-(2-ethoxylbenzamido)-4-methyl-1-n-propyl-1H-pyrrolo-3-formamide (4b)

A mixture of N-(3-cyano-4-methyl-1H-pyrrol-2-yl)-2-ethoxylbenzamide (3a) (2.00 g, 7.44 mmol) or N-(3-cyano-4-methyl-1-n-propyl-1H-pyrrol-2-yl)-2-ethoxylbenzamide (3b) (2.30 g, 7.44 mmol) of preparation 1 and 85% phosphoric acid (14.8 ml) was stirred for 20 minutes at 130° C., cooled and poured into crushed ice (80 g). The precipitations were filtered and dried to give dark red solid of compound (3a) or (3b) with the yield of 80%. The product (3a) and (3b) of this step may be directly used for the next step without further purification.

Preparation 3

2-(2-ethxoylphenyl)-5-methyl-3,7-dihydropyrrolo[2,3-d]pyrimidin-4-one (5) and 2-(2-ethoxyphenyl)-5-methyl-7-n-propyl-3,7-dihydropyrrolo[2,3-d]pyrimidin-4-one (6)

A mixture of 2-(2-ethoxylbenzamido)-4-methyl-1H-pyrrolo-3-formamide (4a) (7.0 g, 25.5 mmol) of preparation 2 and dimethyl cyclohexylamine (20 ml) was refluxed with agitation for 11 hours in N,N-dimethyl formamide (100 ml). After evaporation the solvent by distillation under reduced pressure, the residual was extracted with dichloromethane, and the dichloromethane extraction was washed with water. The resultant extraction was dried with anhydrous sodium sulfate. n-hexane (80 ml) was added into the residual and ground to give product (5) (6.0 g) by filtration with the yield of 91%.

mp 219~221° C.

IR ($cm^{-1}$): 3187, 3114, 3062, 2978, 2923, 1658, 1587, 1460, 1321, 1292, 1250, 1044, 771, 763;

$^1$H NMR (DMSO-$d_6$): δ 1.35 (t, J=6.9 Hz, 3H), 2.29 (s, 3H), 4.13 (q, J=7.0 Hz, 2H), 6.79 (s, 1H), 7.05 (t, 1H), 7.14 (d, 1H), 7.45 (dd, 1H), 7.76 (dd, 1H), 11.35 (brs, 1H), 11.54 (brs, 1H);

$^{13}$C NMR (DMSO-$d_6$): 6 ($CH_3$) 11.2, 14.5; ($CH_2$) 64.2; (CH) 113.0, 118.0, 120.6, 130.1, 131.9, (C) 105.0, 113.6, 121.9, 148.5, 149.8, 156.5, 159.2;

MS ($ES^+$): m/z 287 (M+$NH_4$).

The compound (6) was prepared from compound (4b) according to the above-mentioned method with the yield of 85%.

mp 124~127° C.

IR ($cm^{-1}$): 3234, 3184, 3141, 3103, 3056, 2956, 2943, 2869, 1654, 1595, 1567, 1468, 1311, 1267, 1243, 1191, 1118, 1047, 7580

$^1$H NMR (CDCl$_3$): δ0.88 (t, J=7.5 Hz, 3H), 1.23 (t, 3H), 1.80 (q, 2H), 2.42 (s, 3H), 4.08 (t, J=7.2 Hz, 2H), 4.22 (q, 2H), 6.60 (s, 1H), 7.01 (d, J=8.3 Hz, 1H), 7.08 (t, 1H), 7.40 (m, 1H), 8.35 (dd, J=8.0 and 1.9 Hz, 1H), 11.02 (brs, 1H).

Preparation 4

2-(2-ethxoylphenyl)-5-methyl-7-n-propyl-3,7-dihydro-pyrrolo[2,3-d]pyrimidin-4-one (6)

A mixture of compound (5) (1.5 g, 5.57 mmol) of preparation 3, n-propyl bromide (2.0 g, 16.3 mmol) and potassium carbonate (5 g, 36.2 mmol) was dissolved in acetone (15 ml), refluxed with agitation by heating for 15 hours, after the solids were filtered out, the filtrate was dried under reduced pressure. The resultant was developed by column chromatography, using dichloromethane as mobile phase to obtain 0.6 g of product (6) with yield of 35%. The physical/chemical data were identical with that of the above-mentioned.

Preparation 5

4-ethoxyl-3-(5-methyl-4-oxy-7-n-propyl-4,7-dihydropyrrolo[2,3-d]pyrimidin-2-yl)benzenesulfonyl chloride (7)

2-(2-ethoxylphenyl)-5-methyl-7-n-propyl-3,7-dihydropyrrolo[2,3-d]pyrimidin-4-one (6) (1.25 g, 4.01 mmol) of preparation 4 was added into chlorosulfonic acid (4 ml) that was dissolved in acetic ether (20 ml), stirred at 0° C. by two batches. The obtained solution was stirred at 0° C. for 30 minutes, and then reacted with agitation at room temperature for 3 hours. The resultant solution was poured into the a mixture of icy water (50 ml) and acetic ether (50 ml). The organic layer was separated, washed with cold water (5 ml), desiccated with anhydrous sodium sulfate and concentrated to dryness to afford 1.33 g of product as yellow foam. The yield was 81%. The product was used directly for the next reaction.

Compound 1

2-[2-ethoxyl-5-(4-ethyl-piperazinyl-1-sulfonyl)phenyl]-5-methyl-7-n-propyl-3,7-dihydropyrrolo[2,3-d]pyrimidin-4-one (8)

4-ethoxyl-3-(5-methyl-4-oxy-7-n-propyl-4,7-dihydro-3H-pyrrolo[2,3-d]pyrimidin-2-yl)benzenesulfonyl chloride (7) (1.00 g, 2.44 mmol) of Preparation 5 was dissolved into dichloromethane (20 ml), stirred at 0° C., into which 1-ethyl piperazine (0.78 ml, 6.10 mmol) was added slowly. Reactant solution was stirred at 0° C. for 5 minutes, and then sequentially stirred at room temperature for 5 hours. The crude product was washed with water and dried with anhydrous sodium sulfate to give 1.2 g of product as yellow foam. Continuously, the product was refined by column chromatography (acetic ether:methanol=20:1) to afford 0.89 g of product as a yellow solid with yield of 75%.

mp: 174~176° C. (EtOAc);

IR ($cm^{-1}$): 3324, 2960, 2923, 2869, 2862, 2767, 1682, 1560, 1458, 1355, 1282, 1247, 1172, 1149, 739, 615, 588, 555;

$^1$H NMR (CDCl$_3$): δ0.89 (t, J=7.4 Hz, 3H), 0.99 (t, J=7.2 Hz 3H), 1.61 (t, J=7.0 Hz, 3H), 1.77-1.86 (m, 2H), 2.35 (m, 2H), 2.41 (s, 3H), 2.50 (brs, 4H), 3.05 (brs, 4H), 4.08 (t, J=7.0 Hz 2H), 4.29-4.37 (q, 2H), 6.61 (s, 1H), 7.11 (d, J=8.8 Hz, 1H), 7.77 (dd, J=8.7 and 2.2 Hz, 1H), 8.74 (d, J=2.2, 1H), 10.63 (brs, 1H);

$^{13}$C NMR (CDCl$_3$): δ(CH3) 11.0, 11.3, 11.8, 14.3; (CH2) 23.8, 45.9, 46.1, 51.6, 51.7, 65.8; (CH) 112.9, 121.1, 130.6, 131.3; (C) 105.7, 114.6, 121.4, 127.8, 146.8, 147.3, 159.3, 159.6;

MS ($ES^+$): m/z 505 (M+$NH_4$).

Elemental analysis ($C_{24}H_{33}N_5O_4S$): theoretical value C, 59.12%; H, 6.82%; N, 14.36%; practically measured value C, 59.38%; H, 7.10%; N, 14.12%.

Compound 1-HCl

2-[2-ethoxyl-5-(4-ethylpiperazinyl-1-sulfonyl)phenyl]-5-methyl-7-n-propyl-3,7-dihydropyrrolo[2,3-d]pyrimidin-4-one monohydrochloride (9)

The free alkali (compound 1) (1.00 g, 2.05 mmol) was dissolved into ether (10 ml) and dichloromethane (10 ml), into which the solution of 4M hydrochloric acid (HCl)-dioxane (0.51 ml, 2.04 mmol) diluted with ethyl ether (10 ml) was dropped with agitation. After completion, the resulting solution was continued to stir at room temperature for 20 minutes, filtrated and dried to give 1.01 g of monohydrochloride with yield of 94%.

mp: 147~150° C.;

IR ($cm^{-1}$): 2964, 2931, 2675, 2599, 2462, 1668, 1574, 1456, 1348, 1167, 933, 588;

¹H NMR (D₂O): δ 0.72 (m, 3H), 1.24 (t, J=7.3 Hz, 3H), 1.45 (m, 3H), 1.59 (m, 2H), 2.04 (s, 3H), 2.77-3.81 (all brs, 8H), 3.20 (q, 2H), 3.75 (m, 2H), 4.20 (m, 2H), 6.62 (m, 1H), 7.17 (m, 1H), 7.73 (m, 1H), 8.22 (s, 1H).

Elemental analysis ($C_{24}H_{33}N_5O_4S \cdot HCl$): theoretical value C, 55.00%; H, 6.54%; N, 13.36%; practically measured value C, 55.28%; H, 6.41%; N, 13.07%.

Compound 1-2HCl

2-[2-ethoxyl-5-(4-ethylpiperazinyl-1-sulfonyl)phenyl]-5-methyl-7-n-propyl-3,7-dihydropyrrolo[2,3-d]pyrimidin-4-one dihydrochloride mp: 177~180° C.;
IR (cm⁻¹): 2962, 2929, 2677, 2597, 2456, 1652, 1569, 1458, 1357, 1276, 1162, 1093, 1027, 939, 731, 582;
¹H NMR (D₂O): δ 0.64 (t, J=7.4 Hz, 3H), 1.23 (t, J=7.3 Hz, 3H), 1.40 (t, J=6.9 Hz, 3H), 1.51 (m, 2H), 1.98 (s, 3H), 2.74 (m, 2H), 3.12 (m, 2H), 3.19 (t, 2H), 3.56 (m, 2H), 3.65 (t, 2H), 3.78 (d, 2H), 4.12 (q, 2H), 6.43 (s, 1H), 7.10 (d, J=9.1 Hz, 1H), 7.68 (dd, J=8.8 and 2.3 Hz, 1H), 8.16 (d, J=2.3 Hz, 1H).

Likewise, by using similar processes, the starting materials were correspondingly used to synthesize the compounds as follows:

Compound 2

2-[2-methoxyl-5-(4-ethylpiperazinyl-1-sulfonyl)phenyl]-5-methyl-7-n-propyl-3,7-dihydropyrrolo[2,3-d]pyrimidin-4-one Compound of 4-methoxyl-3-(5-methyl-4-oxy-7-n-propyl-3,7-dihydropyrrolo[2,3-d]pyrimidin-2-yl)benzenesulfonylchloride (IB) was prepared by using the 2-amino-3-cyano-4-methylpyrrole (IE) and 2-methoxylbenzoyl chloride (IF) as starting materials via the corresponding intermediates ID, IA, IG (IH) and IC. The resulting compound was reacted with 1-ethylpiperazine to give the titled compound.

¹H NMR (CDCl₃): δ 0.86 (t, 3H), 0.99 (t, 3H), 1.73 (m, 2H), 2.32 (q, 2H), 2.40 (s, 3H), 2.48 (brs, 4H), 3.04 (brs, 4H), 4.08 (t, 2H), 4.14 (s, 3H), 6.60 (s, 1H), 7.0 (d, 1H), 7.74 (dd, 1H), 8.77 (d, 1H).

MS (ES): m/z 491 (M+NH₄).

Compound 3

2-[2-n-propyloxy-5-(4-ethylpiperazinyl-1-sulfonyl)phenyl]-5-methyl-7-n-propyl-3,7-dihydropyrrolo[2,3-d]pyrimidin-4-one 4-n-propyloxy-3-(5-methyl-4-oxy-7-n-propyl-3,7-dihydropyrrolo[2,3-d]pyrimidin-2-yl)benzenesulfonylchloride (IB) was prepared by using 2-amino-3-cyano-4-methylpyrrole (IE) and 2-n-propyloxybenzoyl chloride (IF) as starting materials via the corresponding intermediates ID, IA, IG (IH) and IC. The resulting compound was reacted with 1-ethylpiperazine to give the titled compound.

¹H NMR (CDCl₃) δ: 0.87 (t, 3H), 1.00 (t, 3H), 1.16 (t, 3H), 1.79 (m 2H), 2.01 (m, 2H), 2.36 (q, 2H), 2.42 (s, 3H), 2.50 (brs, 4H), 3.04 (brs, 4H), 4.08 (t, 2H), 4.21 (t, 2H), 6.60 (s, 1H), 7.09 (d, 1H), 7.77 (dd, 1H), 8.77 (d, 1H)

MS (ES⁺): m/z 519 (M+NH₄). .

Compound 4

2-[2-allyloxy-5-(4-ethylpiperazinyl-1-sulfonyl)phenyl]-5-methyl-7-n-propyl-3,7-dihydropyrrolo[2,3-d]pyrimidin-4-one 4-allyloxy-3-(5-methyl-4-oxy-7-n-propyl-3,7-dihydropyrrolo[2,3-d]pyrimidin-2-yl)benzenesulfonylchloride (IB) was prepared by using 2-amino-3-cyano-4-methylpyrrole (IE) and 2-allyloxybenzoyl chloride (IF) as starting materials via the corresponding intermediates ID, IA, IG (IH) and IC. The resulting compound was reacted with 1-ethylpiperazine to give the titled compound.

¹H NMR (CDCl₃) δ: 0.83 (t, 3H), 0.97 (t, 3H), 1.82 (, 2H), 2.37 (q, 2H), 2.41 (s, 3H), 2.52 (brs, 4H), 3.07 (brs, 4H), 4.07 (t, 2H), 4.62 (m, 2H), 5.24 (m, 2H), 5.83 (m, 1H), 6.62 (s, 1H), 7.12 (d, 1H), 7.79 (dd, 1H), 8.69 (d, 1H), 9.97 (br, 1H).

MS (ES⁺): m/z 517 (M+NH₄).

Compound 5

2-[2-n-propyloxy-5-(4-ethylpiperazinyl-1-sulfonyl)phenyl]-5-ethyl-7-n-propyl-3,7-dihydropyrrolo[2,3-d]pyrimidin-4-one 4-n-propyloxy-3-(5-ethyl-4-oxy-7-n-propyl-3,7-dihydropyrrolo[2,3-d]pyrimidin-2-yl)-benzenesulfonylchloride (IB) was prepared by using 2-amino-3-cyano-4-ethylpyrrole (IE) and 2-propyloxybenzoyl chloride (IF) as starting materials via the corresponding intermediates ID, IA, IG (IH) and IC. The resulting compound was reacted with 1-ethylpiperazine to give the titled compound.

¹H NMR (CDCl₃) δ: 0.88 (t, 3H), 0.99 (t, 3H), 1.04 (t, 3H), 1.52 (t, 3H), 1.74-1.84 (m, 4H), 2.35 (q, 2H), 2.46 (brs, 4H), 2.68 (q, 2H), 3.05 (brs, 4H), 4.09 (t, 2H), 4.36 (t, 2H), 6.61 (s, 1H), 7.09 (d, 1H), 7.81 (dd, 1H), 8.71 (d, 1H).

MS (ES⁺): m/z 533 (M+NH₄).

Compound 6

2-[2-ethoxyl-5-(4-methylpiperazinyl-1-sulfonyl)phenyl]-5-methyl-7-n-propyl-3,7-dihydropyrrolo[2,3-d]pyrimidin-4-one The titled compound was prepared from the reaction of 4-ethoxyl-3-(5-methyl-4-oxy-7-n-propyl-4,7-dihydropyrrolo[2,3-d]pyrimidin-2-yl)-benzenesulfonylchloride (IB) obtained from previous Preparation 5 and 1-methylpiperazine.

¹H NMR (D₂O): δ: 0.90 (t, 3H), 1.62 (s, 3H), 1.78 (m, 2H), 2.15 (s, 3H), 2.41 (s, 3H), 2.48 (brs, 4H), 3.04 (brs, 4H), 4.08 (t, 2H), 4.34 (q, 2H), 6.61 (s, 1H), 7.09 (d, 1H), 7.74 (dd, 1H), 8.76 (d, 1H).

MS (ES): m/z 491 (M+NH₄).

Compound 7

2-[2-ethoxyl-5-(4-methylpiperazinyl-1-sulfonyl)phenyl]-5-ethyl-7-n-propyl-3,7-dihydropyrrolo[2,3-d]pyrimidin-4-one 4-ethoxyl-3-(5-ethyl-4-chloro-7-n-propyl-3,7-dihydropyrrolo[2,3-d]pyrimidin-2-yl)-benzenesulfonylchloride (IB) was prepared by using 2-amino-3-cyano-4-ethylpyrrole (IE) and 2-ethoxylbenzoyl chloride (IF) as starting materials via the corresponding intermediates ID, IA, IG (IH) and IC. The resulting compound was reacted with 1-methylpiperazine to give the titled compound.

$^1$H NMR (CDCl$_3$) δ: 0.92 (t, 3H), 1.54-1.64 (m, 6H), 1.75 (m, 2H), 2.14 (s, 3H), 2.53 (m, 6H), 3.04 (brs, 4H), 4.09 (t, 2H), 4.37 (q, 2H) 6.62 (s, 1H), 7.11 (d, 1H), 7.80 (dd, 1H), 8.76 (d, 1H).

MS (ES): m/z 505 (M+NH$_4$).

Compound 8

2-[2-ethoxyl-5-(4-ethoxylcarbonylpiperazinyl-1-sulfonyl)phenyl]-5-methyl-7-n-propyl-3,7-dihydro-pyrrolo[2,3-d]pyrimidin-4-one The titled compound was prepared from the reaction of 4-ethoxyl-3-(5-methyl-4-oxy-7-n-propyl-4,7-dihydropyr-rolo[2,3-d]pyrimidin-2-yl)-benzenesulfonylchloride (IB) obtained from previous Preparation 5 and 1-ethoxylcarbon-ylpiperazine.

$^1$H NMR (CDCl$_3$) δ: 0.90 (t, 3H), 1.25 (t, 3H), 1.62 (t, 3H), 1.83 (m, 2H), 2.41 (s, 3H), 2.48 (brs, 4H), 3.07 (brs, 4H), 4.05 (q, 2H), 4.32 (q, 2H), 4.41 (q, 2H), 6.62 (s, 1H), 7.12 (d, 1H), 7.81 (d, 1H), 8.67 (s, 1H).

MS (ES$^+$): m/z 549 (M+NH$_4$).

Compound 9

2-[2-ethoxyl-5-(4-(2-hydroxyethyl)piperazinyl-1-sulfonyl)phenyl]-5-methyl-7-n-propyl-3,7-dihydro-pyrrolo[2,3-d]pyrimidin-4-one The titled compound was prepared from the reaction of 4-ethoxyl-3-(5-methyl-4-oxy-7-n-propyl-4,7-dihydropyr-rolo[2,3-d]pyrimidin-2-yl)-benzenesulfonylchloride (IB) of Preparation 5 and 1-(2-hydroxyethyl)piperazine.

$^1$H NMR (CDCl$_3$) δ: 0.89 (t, 3H), 1.61 (t, 3H), 1.72 (m, 2H), 2.41 (s, 3H), 2.49-2.58 (m, 6H), 3.07 (brs, 4H), 3.67 (m, 2H), 4.08 (t, 2H), 4.33 (q, 2H), 6.61 (s, 1H), 7.10 (d, 1H), 7.76 (dd, 1H), 8.69 (d, 1H).

MS (ES$^+$): m/z 521 (M+NH$_4$).

Compound 10

2-[2-ethoxyl-5-(pyrrolidinyl-1-sulfonyl)phenyl]-5-methyl-7-n-propyl-3,7-dihydropyrrolo[2,3-d]pyrimi-din-4-one The titled compound was prepared from the reaction of 4-ethoxyl-3-(5-methyl-4-oxy-7-n-propyl-4,7-dihydropyr-rolo[2,3-d]pyrimidin-2-yl)-benzenesulfonylchloride (IB) of Preparation 5 and pyrrolidine.

$^1$H NMR (CDCl$_3$) δ: 0.89 (t, 3H), 1.61 (t, 3H), 1.81 (m, 6H), 2.41 (s, 3H), 3.25 (m, 4H), 4.10 (t, 2H), 4.34 (q, 2H), 6.62 (s, 1H), 7.12 (d, 1H), 7.85 (dd, 1H), 8.83 (t, 1H), 10.76 (brs, 1H).

MS (ES$^+$): m/z 462 (M+NH$_4$).

Compound 11

2-{2-ethoxyl-5-[3-(2-oxy-pyrrolidinyl-1)-n-propy-lamino-N-sulfonyl]phenyl}-5-methyl-7-n-propyl-3,7-dihydropyrrolo[2,3-d]pyrimidin-4-one The titled compound was prepared from the reaction of 4-ethoxyl-3-(5-methyl-4-oxy-7-n-propyl-4,7-dihydropyr-rolo[2,3-d]pyrimidin-2-yl)benzenesulfonylchloride (IB) of Preparation 5 and 3-(2-oxy-pyrrolidinyl-1)-n-propylamine.

$^1$H NMR (CDCl$_3$) δ: 0.90 (t, 3H), 1.55 (t, 2H), 1.68 (m, 2H), 1.78 (m, 2H), 1.94 (t, 2H), 2.27 (t, 2H), 2.38 (s, 3H), 2.87 (t, 2H), 3.28 (m, 4H) 4.07 (t, 2H), 4.30 (t, 2H), 6.30 (m, 1H), 6.60 (s, 1H), 7.08 (d, 1H), 7.88 (dd, 1H), 8.79 (d, 1H), 10.79 (brs, 1H).

MS (ES$^+$): m/z 533 (M+NH$_4$).

Compound 12

2-{2-ethoxyl-5-[2-(pyrrolidinyl-1)ethylamino-N-sulfonyl]phenyl}-5-methyl-7-n-propyl-3,7-dihydro-pyrrolo[2,3-d]pyrimidin-4-one The titled compound was prepared from the reaction of 4-ethoxyl-3-(5-methyl-4-oxy-7-n-propyl-4,7-dihydropyr-rolo[2,3-d]pyrimidin-2-yl)-benzenesulfonylchloride (IB) of Preparation 5 and 2-(pyrrolidinyl-1)ethylamine.

$^1$H NMR (CDCl$_3$) δ: 0.89 (t, 3H), 1.59 (t, 3H), 1.64 (brs, 4H), 1.81 (q, 2H), 2.33 (brs, 4H), 2.41 (s, 3H), 2.52 (t, 2H), 3.01 (t, 2H), 4.09 (t, 2H), 4.33 (q, 2H), 6.60 (s, 1H), 7.09 (d, 1H), 7.89 (dd, 1H), 8.84 (s, 1H).

MS (ES$^+$): m/z 505 (M+NH$_4$).

Compound 13

2-[2-ethoxyl-5-(morpholino-4-sulfonyl)phenyl]-5-methyl-7-n-propyl-3,7-dihydropyrrolo[2,3-d]pyrimi-din-4-one 2-[2-ethoxyl-5-(morpholino-4-sulfonyl)phenyl]-5-methyl-3,7-dihydropyrrolo[2,3-d]pyrimidin-4-one (IG) was prepared from the reaction of 2-amino-3-cyano-4-methylpy-ridine (IE) and 2-ethoxyl-1-(morpholino-4-sulfonyl)benzoyl chloride (IF) via the corresponding intermediate (ID). The resulting compound was reacted with n-propyl bromide (IH) to give the titled compound.

$^1$H NMR (CDCl$_3$) δ: 0.91 (t, 3H), 1.64 (t, 3H), 1.80 (m, 2H), 2.42 (s, 3H), 3.03 (m, 4H), 3.74 (m, 4H), 4.10 (t, 2H), 4.39 (q, 2H), 6.66 (s, 1H), 7.15 (d, 1H), 7.80 (dd, 1H), 8.77 (d, 1H), 10.89 (brs, 1H).

MS (ES$^+$): m/z 478 (M+NH$_4$).

Compound 14

2-[2-ethoxyl-5-(3-(morpholino-4)-n-propylamino-N-sulfonyl)phenyl]-5-methyl-7-n-propyl-3,7-dihydro-pyrrolo[2,3-d]pyrimidin-4-one The titled compound was prepared from the reaction of 4-ethoxyl-3-(5-methyl-4-oxy-7-n-propyl-4,7-dihydropyr-rolo[2,3-d]pyrimidin-2-yl)-benzenesulfonylchloride (IB) of Preparation 5 and 3-(morpholino-4)-n-propylamine.

$^1$H NMR (CDCl$_3$) δ: 0.92 (t, 3H), 1.59 (t, 3H), 1.72 (m, 2H), 1.84 (q, 2H), 2.43 (s, 3H), 2.40-2.50 (m, 6H), 3.11 (t, 2H), 3.72 (m, 4H), 4.11 (t, 2H), 4.32 (q, 2H), 6.60 (s, 1H), 7.13 (t, 1H), 7.88 (d, 1H), 8.79 (s, 1H), 9.95 (brs, 1H).

MS (ES$^+$): m/z 535 (M+NH$_4$).

Compound 15

2-[2-ethoxyl-5-(2-(morpholino-4)-ethylamino-N-sulfonyl)phenyl]-5-methyl-7-n-propyl-3,7-dihydro-pyrrolo[2,3-d]pyrimidin-4-one The titled compound was prepared from the reaction of 4-ethoxyl-3-(5-methyl-4-oxy-7-n-propyl-4,7-dihydropyrrolo[2,3-d]pyrimidin-2-yl)-benzenesulfonylchloride (IB) of Preparation 5 and 2-(morpholino-4)ethylamine.

¹H NMR (CDCl₃) δ: 0.90 (t, 3H), 1.58 (t, 3H), 1.80 (m, 2H), 2.32 (m, 4H), 2.44 (s, 3H), 2.74 (t, 2H), 3.03 (t, 2H), 3.58 (m, 4H), 4.06 (t, 2H), 4.30 (q, 2H), 6.62 (s, 1H), 7.08 (d, 1H), 7.87 (d, 1H), 8.79 (d, 1H), 10.82 (brs, 1H).

MS (ES⁺): m/z 521 (M+NH₄).

Compound 16

2-[2-ethoxyl-5-(2,6-dimethylmorpholino-N-sulfonyl) phenyl]-5-methyl-7-n-propyl-3,7-dihydropyrrolo[2,3-d]pyrimidin-4-one 2-[2-ethoxyl-5-(2,6-dimethylmorpholino-4-sulfonyl)phenyl]-5-methyl-3,7-dihydropyrrolo[2,3-d]pyrimidin-4-one (IG) was prepared, from the reaction of 2-amino-3-cyano-4-methylpyrrole (IE) and 2-ethoxyl-5-(2,6-dimethylmorpholino-4-sulfonyl)benzoyl chloride (IF) via the corresponding intermediate ID. The resulting compound was reacted with n-propyl bromide (IH) to give the titled compound.

¹H NMR (CDCl₃) δ: 0.87 (t, 3H), 1.09 (s, 3H), 1.11 (s, 3H), 1.61 (t, 3H), 1.80 (m, 2H), 1.96 (t, 2H), 2.39 (s, 3H), 3.53 (s, 1H), 3.58 (s, 1H), 3.70 (m, 2H), 4.08 (t, 2H), 4.33 (q, 2H), 6.60 (s, 1H), 7.10 (d, 1H), 7.77 (dd, 1H), 8.69 (d, 1H), 10.76 (br, 1H).

MS (ES⁺): m/z 506 (M+NH₄).

Compound 17

2-[2-ethoxyl-5-(benzylpiperidyl-4-aminosulfonyl) phenyl]-5-methyl-7-n-propyl-3,7-dihydropyrrolo[2,3-d]pyrimidin-4-one The titled compound was prepared from the reaction of 2-ethoxyl-5-(1-benzylpiperidyl-4-aminosulfonyl)benzoyl chloride (IF) and 1-n-propyl-2-amino-3-cyano-4-methylpyrrole (IE).

¹H NMR (CDCl₃) δ: 0.82 (t, 3H), 1.50-1.80 (m, 9H), 2.01 (m, 2H), 2.40 (s, 3H), 2.76 (m, 2H), 3.14 (m, 1H), (s, 2H), 3.99 (t, 2H), 4.23 (q, 2H), 6.58 (s, 1H), 6.94 (d, 1H), 7.21-7.27 (m, 5H), 7.84 (dd, 1H), 8.75 (d, 1H).

MS (ES⁺): m/z 581 (M+NH₄).

Compound 18

2-[2-ethoxyl-5-(2-(piperidin-1-yl)ethylamine-1-sulfonyl)phenyl]-5-methyl-7-n-propyl-3,7-dihydropyrrolo[2,3-d]pyrimidin-4-one The titled compound was prepared from the reaction of 4-ethoxyl-3-(5-methyl-4-oxy-7-n-propyl-4,7-dihydropyrrolo[2,3-d]pyrimidin-2-yl)benzenesulfonylchloride (IB) of Preparation 5 and 2-(piperidin-1-yl)ethylamine.

¹H NMR (CDCl₃) δ: 0.89 (t, 3H), 1.40 (m, 2H), 1.50-1.70 (m, 7H), 1.79 (m 2H), 2.38 (s, 3H), 2.57 (brs, 4H), 2.65 (t, 2H), 3.07 (t, 2H), 4.08 (t, 2H), 4.29 (q, 2H), 6.61 (s, 1H), 7.08 (d, 1H), 7.87 (d, 1H), 8.77 (s, 1H).

MS (ES⁺): m/z 519 (M+NH₄).

Compound 19

2-[2-ethoxyl-5-(4-benzylpiperazinyl-1-sulfonyl)phenyl]-5-methyl-7-n-propyl-3,7-dihydropyrrolo[2,3-d]pyrimidin-4-one The titled compound was prepared from the reaction of 2-ethoxyl-5-(4-benzylpiperazinyl-1-sulfonyl)benzoyl chloride (IF) and 1-n-propyl-2-amino-3-cyano-4-methylpyrrole (IE) via intermediate ID.

¹H NMR (CDCl₃) δ: 0.97 (t, 3H), 1.62 (t, 3H), 1.80 (m, 2H), 2.41 (s, 3H), 2.60 (m, 4H), 2.63 (s, 2H), 3.09 (m, 4H), 4.07 (t, 2H), 4.35 (q, 2H), 6.61 (s, 1H), 7.10 (d, 1H), 7.21-7.29 (m, 5H), 7.78 (dd, 1H), 8.78 (d, 1H), 10.64 (brs, 1H).

MS (ES⁺): m/z 567 (M+NH₄).

Compound 20

2-[2-ethoxyl-5-(4-phenylpiperazinyl-1-sulfonyl)phenyl]-5-methyl-7-n-propyl-3,7-dihydropyrrolo[2,3-d]pyrimidin-4-one 1-n-propyl-2-(2-ethoxyl-5-(4-phenylpiperazinyl-1-sulfonyl)benzoyl amino)-4-methyl-1H-pyrrolo-3-formamide (1A) was prepared from the reaction of 1-n-propyl-2-amino-3-cyano-4-methylpyrrole (IE) and 2-ethoxyl-5-(4-benzylpiperidinyl-1-sulfonyl)benzoyl chloride (IF) via the intermediate ID. A cyclization reaction of IA was effectively carried out to give the titled compound.

¹H NMR (CDCl₃) δ: 0.91 (t, 3H), 1.64 (t, 3H), 1.82 (m, 2H), 2.41 (s, 3H), 3.29 (m, 8H), 4.11 (t, 2H), 4.36 (q, 2H), 6.63 (s, 1H), 6.84-7.05 (m, 2H), 7.14 (d, 1H), 7.20-7.30 (m, 3H), 7.84 (dd, 1H), 8.82 (d, 1H), 10.64 (brs, 1H).

MS (ES⁺): m/z 553 (M+NH₄).

Compound 21

2-[2-ethoxyl-5(piperazinyl-1-sulfonyl)phenyl]-5-methyl-7-n-propyl-3,7-dihydropyrrolo[2,3-d]pyrimidin-4-one The titled compound was prepared from the reaction of 4-ethoxyl-3-(5-methyl-4-oxy-7-n-propyl-4,7-dihydropyrrolo[2,3-d]pyrimidin-2-yl)-benzenesulfonylchloride (IB) and excess amount of piperazine.

¹H NMR (CDCl₃) δ: 0.91 (t, 3H), 1.60 (t, 3H), 1.77-1.86 (m, 2H), 2.41 (s, 3H), 2.47 (brs, 4H), 2.96 (brs, 4H), 4.08 (t, 2H), 4.29-4.35 (q, 2H), 6.61 (s, 1H), 7.14 (d, 1H), 7.80 (dd, 1H), 8.70 (d, 1H), 10.68 (s, 1H).

MS (ES⁺): m/z 477 (M+NH₄).

Compound 22

2-[2-ethoxyl-5-(4-benzo[1,3]dioxol-5-yl-methylpiperazinyl-1-sulfonyl)phenyl]-5-methyl-7-n-propyl-3,7-dihydropyrrolo[2,3-d]pyrimidin-4-one 1-n-propyl-2-(2-ethoxyl-5-(4-benzo[1,3]dioxol-5-yl-methylpiperazinyl-1-sulfonyl)benzoylamino)-4-methyl-1H-pyrrolo-3-formamide (IA) was prepared from the reaction of 1-n-propyl-2-amino-3-cyano-4-methylpyrrole (IE) and 2-ethoxyl-5-(4-benzo[1,3]dioxol-5-yl-methylpiperazinyl-1-sulfonyl)benzoyl chloride (IF) via the intermediate ID. A cyclization reaction of IA was effectively carried out to give the titled compound.

¹H NMR (CDCl₃) δ: 0.87 (t, 3H), 1.63 (t, 3H), 1.76 (m, 2H), 2.41 (s, 3H), 2.51 (brs, 4H), 3.08 (brs, 4H), 3.38 (s, 2H), 4.08 (t, 2H), 4.34 (q, 2H), 5.89 (s, 2H), 6.61 (s, 1H), 6.62-6.80 (m, 3H), 7.11 (d, 1H), 7.75 (dd, 1H), 8.76 (d, 1H), 10.64 (s, 1H).

MS (ES⁺): m/z 611 (M+NH₄).

Compound 23

2-{2-ethoxyl-5-[4-(3-phenyl-n-propan-1-yl)piperidyl-1-sulfonyl]phenyl}-5-methyl-7-n-propyl-3,7-dihydropyrrolo[2,3-d]pyrimidin-4-one The titled compound was prepared from the reaction of 4-ethoxyl-3-(5-methyl-4-oxy-7-n-propyl-4,7-dihydropyrrolo[2,3-d]pyrimidin-2-yl)-benzenesulfonylchloride (IB) of Preparation 5 and 4-(3-phenyl-n-propan-1-yl)piperidine.

¹H NMR (CDCl₃) δ: 0.90 (t, 3H), 1.23-1.31 (m, 5H), 1.50-1.85 (m, 9H), 2.25 (t, 2H), 2.41 (s, 3H), 2.52 (m, 2H), 3.77 (d, 2H), 4.09 (t, 2H), 4.34 (q, 2H), 6.61 (s, 1H), 7.08-7.29 (m, 6H), 7.80 (dd, 1H), 8.78 (d, 1H).

MS (ES⁺): m/z 594 (M+NH₄).

Compound 24

2-[2-ethoxyl-5-(n-propylamino-1-sulfonyl)phenyl]-5-methyl-7-n-propyl-3,7-dihydropyrrolo[2,3-d]pyrimidin-4-one 4-ethoxyl-3-(5-ethyl-4-oxy-7-n-propyl-3,7-dihydropyrrolo[2,3-d]pyrimidin-2-yl)benzenesulfonylchloride (IB) was prepared from the reaction of 1-n-propyl-2-amino-3-cyano-4-ethylpyrrole (IE) and 2-ethoxyl benzoyl chloride (IF) via the corresponding intermediates ID, IA and IC. The resulting compound was reacted with n-propylamine to give the titled compound.

¹H NMR (CDCl₃) δ: 0.94-0.99 (m, 6H), 1.52 (q, 2H), 1.61 (t, 3H), 1.77 (m, 2H), 2.40 (s, 3H), 2.92 (brs, 2H), 4.09 (t, 2H), 4.34 (q, 2H), 4.82 (brs, 1H), 6.64 (s, 1H), 7.08 (d, 1H), 7.89 (dd, 1H), 8.83 (d, 1H), 10.90 (brs, 1H).

MS (ES⁺): m/z 450 (M+NH₄).

Compound 25

2-[2-ethoxyl-5-(N,N-di(2-hydroxyethyl)aminosulfonyl)phenyl]-5-methyl-7-n-propyl-3,7-dihydropyrrolo[2,3-d]pyrimidin-4-one 4-ethoxyl-3-(5-ethyl-4-oxy-7-n-propyl-3,7-dihydropyrrolo[2,3-d]pyrimidin-2-yl)benzenesulfonylchloride (IB) was prepared from the reaction of 1-n-propyl-2-amino-3-cyano-4-ethylpyrrole (IE) and 2-ethoxyl benzoyl chloride (IF) via the corresponding intermediates ID, IA and IC. The resulting compound was reacted with N,N-di(2-hydroxyethyl)amine to give the titled compound.

¹H NMR (CDCl₃) δ: 0.90 (t, 3H), 1.58 (t, 3H), 1.78 (m, 2H), 2.39 (s, 3H), 3.32 (t, 4H), 3.85 (t, 4H), 4.10 (t, 2H), 4.35 (q, 2H), 6.64 (s, 1H), 7.10 (d, 1H), 7.85 (dd, 1H), 8.79 (d, 1H), 10.84 (brs, 1H).

MS (ES⁺): m/z 496 (M+NH₄).

Compound 26

2-{2-ethoxyl-5-[N-(2-hydroxyethyl)-N-methyl]aminosulfonyl}phenyl}-5-m ethyl-7-n-propyl-3,7-dihydropyrrolo[2,3-d]pyrimidin-4-one 4-ethoxyl-3-(5-ethyl-4-oxy-7-n-propyl-3,7-dihydropyrrolo[2,3-d]pyrimidin-2-yl)benzenesulfonylchloride (IB) was prepared from the reaction of 1-n-propyl-2-amino-3-cyano-4-ethylpyrrole (IE) and 2-ethoxyl benzoyl chloride (IF) via the corresponding intermediates ID, IA and IC. The resulting compound was reacted with N-(2-hydroxyethyl)-N-methylamine to give the titled compound.

¹H NMR (CDCl₃) δ: 0.90 (t, 3H), 1.62 (t, 3H), 1.78 (m, 2H), 2.41 (s, 3H), 2.87 (s, 3H), 3.20 (t, 2H), 3.77 (t, 2H), 4.10 (t, 2H), 4.35 (q, 2H), 6.65 (s, 1H), 7.14 (d, 1H), 7.85 (dd, 1H), 8.79 (d, 1H), 10.89 (brs, 1H).

MS (ES⁺): m/z 466 (M+NH₄).

Compound 27

2-{2-ethoxyl-5-[N-(2-hydroxyethyl-N-ethyl)aminosulfonyl]phenyl}-5-methyl-7-n-propyl-3,7-dihydropyrrolo[2,3-d]pyrimidin-4-one 4-ethoxyl-3-(5-ethyl-4-oxy-7-n-propyl-3,7-dihydropyrrolo[2,3-d]pyrimidin-2-yl)benzenesulfonylchloride (IB) was prepared from the reaction of 1-n-propyl-2-amino-3-cyano-4-ethylpyrrole (IE) and 2-ethoxyl benzoyl chloride (IF) via the corresponding intermediates ID, IA and IC. The resulting compound was reacted with N-(2-hydroxyethyl)-N-ethylamine to give the titled compound.

¹H NMR (CDCl₃) δ: 0.90 (t, 3H), 1.18 (t, 3H), 1.62 (t, 3H), 1.79 (m, 2H), 2.41 (s, 3H), 3.30 (m, 4H), 3.75 (t, 2H), 4.08 (t, 2H), 4.32 (q, 2H), 6.61 (s, 1H), 7.10 (d, 1H), 7.86 (d, 1H), 8.81 (d, 1H), 10.69 (brs, 1H).

MS (ES⁺): m/z 480 (M+NH₄).

Compound 28

2-{2-ethoxyl-5-[N-(2-hydroxyethyl)-N-n-butyl]aminosulfonyl}phenyl}-5-methyl-7-n-propyl-3,7-dihydropyrrolo[2,3-d]pyrimidin-4-one The titled compound was prepared from the reaction of 4-ethoxyl-3-(5-methyl-4-oxy-7-n-propyl-4,7-dihydropyrrolo[2,3-d]pyrimidin-2-yl)benzenesulfonylchloride (IB) of Preparation 5 and N-(2-hydroxyethyl)-N-n-butylamine.

¹H NMR (CDCl₃) δ: 0.85-0.93 (m, 6H), 1.29-1.40 (t, 2H), 1.49-1.65 (m, 35), 1.82, 2H), 2.40 (s, 3H), 3.15-3.30 (m, 4H), 3.78 (t, 2H), 4.11 (t, 2H), 4.38 (q, 2H), 6.66 (s, 1H), 7.12 (d, 1H), 7.88 (dd, 1H), 8.82 (d, 1H), 10.96 (brs, 1H).

MS (ES⁺): m/z 508 (M+NH₄).

Compound 29

2-{2-ethoxyl-5-(p-ethoxylcarboxylphenylamino)-N-sulfonyl}phenyl}-5-methyl-7-n-propyl-3,7-dihydropyrrolo[2,3-d]pyrimidin-4-one 2-[2-ethoxyl-5-(p-ethoxylcarboxylphenylamino-N-sulfonyl)phenyl]-5-methyl-3,7-dihydropyrrolo[2,3-d]pyrimidin-4-one (IG) was prepared from the reaction of 2-amino-3-cyano-4-methylpyrrole (IE) and 2-ethoxyl-5-(p-ethoxylcarboxylphenylamino)-N-sulfonyl)benzoyl chloride (IF) via the corresponding intermediates ID and IA. The resulting compound was reacted with n-propyl bromine (IH) to give the titled compound.

¹H NMR (CDCl₃) δ: 0.82 (t, 3H), 1.31 (t, 3H), 1.49 (t, 3H), 1.74 (m, 2H), 2.40 (s, 3H), 43.95 (t, 2H), 4.16-4.32 (m, 4H), 6.60 (m, 3H), 6.90 (d, 1H), 7.25 (d, 2H), 7.79-7.90 (m, 3H), 8.70 (d, 1H), 8.97 (s, 1H), 10.83 (s, 1H).

MS (ES⁺): m/z 566 (M+NH₄).

Compound 30

2-{2-ethoxyl-5-(o-benzoylphenylamino)-N-sulfonyl}phenyl}-5-methyl-7-n-propyl-3,7-dihydropyrrolo[2,3-d]pyrimidin-4-one The titled compound was prepared from the reaction of 4-ethoxyl-3-(5-methyl-4-oxy-7-n-propyl-4,7-dihydropyrrolo[2,3-d]pyrimidin-2-yl)-benzenesulfonylchloride (IB) of Preparation 5 and o-benzoyl phenylamine.

¹H NMR (CDCl₃) δ: 0.91 (t, 3H), 1.52 (t, 3H), 1.78 (m, 2H), 2.41 (s, 3H), 4.02 (t, 2H), 4.13 (m, 2H), 6.63 (s, 1H), 6.80 (d, 1H), 7.0-7.55 (m, 7H), 7.72 (dd, 1H), 7.80 (d, 2H), 8.54 (d, 1H), 9.79 (s, 1H0, 10.62 (brs, 1H).
MS (ES⁺): m/z 588 (M+NH₄).

Compound 31

2-{2-ethoxyl-5-(N2-acethydrazido)-N-1-sulfonyl}phenyl}-5-methyl-7-n-propyl-3,7-dihydro-pyrrolo[2,3-d]pyrimidin-4-one The titled compound was prepared from the reaction of 4-ethoxyl-3-(5-methyl-4-oxy-7-n-propyl-4,7-dihydropyrrolo[2,3-d]pyrimidin-2-yl)-benzenesulfonylchloride (IB) of Preparation 5 and acethydrazide.
¹H NMR (CDCl₃) δ☐0.90 (t, 3H), 1.56 (t, 3H), 1.79 (m, 2H), 1.90 (s, 3H), 2.39 (s, 3H), 4.09 (t, 2H), 4.27 (q, 2H), 6.67 (s, 1H), 7.01 (d, 1H), 7.52 (brs, 1H0, 7.9 (dd, 1H), 8.74 (m, 2H).
MS (ES⁺): m/z 465 (M+NH₄).

Compound 32

2-{2-ethoxyl-5-(2-dimethylaminoethylamino)-N-sulfonyl}phenyl}-5-methyl-7-n-propyl-3,7-dihydro-pyrrolo[2,3-d]pyrimidin-4-one The titled compound was prepared from the reaction of 4-ethoxyl-3-(5-methyl-4-oxy-7-n-propyl-4,7-dihydropyrrolo[2,3-d]pyrimidin-2-yl)-benzenesulfonylchloride (IB) obtained from previous Preparation 5 and 2-dimethylaminoethylamine.
¹H NMR (CDCl₃) δ: 0.90 (t, 3H), 1.61 (t, 3H), 1.80 (m, 2H), 2.09 (m, 6H), 2.36 (t, 2H), 2.40 (s, 3H), 3.02 (t, 2H), 4.10 (t, 2H), 4.34 (q, 2H), 6.61 (s, 1H), 7.11 (d, 1H), 7.90 (dd, 1H), 8.83 (d, 1H).
MS (ES⁺): m/z 479 (M+NH₄).

Compound 33

2-{2-ethoxyl-5-(4-ethylpiperazinyl-1-sulphonyl)phenyl}-5-ethyl-7-n-propyl-3,7-dihydropyrrolo[2,3-d]pyrimidin-4-one 4-ethoxyl-3-(5-ethyl-4-oxy-7-n-propyl-3,7-dihydropyrrolo[2,3-d]pyrimidin-2-yl)benzenesulfonylchloride (IB) was prepared from the reaction of 2-amino-3-cyano-4-ethylpyrrole (IE) and 2-ethoxylbenzoyl chloride (IF) via the corresponding intermediates ID, IA, IG (IH) and IC. The resulting compound was reacted with 1-ethylpiperazine to give the titled compound.
¹H NMR (CDCl₃) δ: 0.90-0.95 (m, 6H), 1.56-1.60 (m, 6H), 1.75 (m, 2H), 2.49 (brs, 4H), 2.53 (q, 2H), 3.06 (m, 4H), 4.05 (q, 2H), 4.34 (q, 2H), 6.61 (s, 1H), 7.10 (d, 1H), 7.75 (dd, 1H), 8.79 (d, 1H), 9.90 (br, 1H).
MS (ES⁺): m/z 519 (M+NH₄).

Compound 34

2-[2-ethoxyl-5-(4-ethylpiperazinyl-1-sulphonyl)phenyl]-5-morpholinomethyl-7-n-propyl-3,7-dihydropyrrolo[2,3-d]pyrimidin-4-one 4-ethoxyl-3-(5-morpholinomethyl-4-oxy-7-n-propyl-3,7-dihydropyrrolo[2,3-d]pyrimidin-2-yl)benzenesulfonylchloride (IB) was prepared from the reaction of 2-amino-3-cyano-4-morpholinomethylpyrrole (IE) and 2-ethoxyl benzoyl chloride (IF) via the corresponding intermediates ID, IA, IG (IH) and IC. The resulting compound was reacted with 1-ethylpiperazine to give the titled compound.
¹H NMR (CDCl₃) δ: 0.90-1.00 (m, 6H), 1.61 (t, 3H), 1.74 (m, 2H), 2.32-2.56 (m, 8H), 3.06 (m, 4H), 3.67 (m, 4H), 3.94 (s, 2H), 4.07 (t, 2H), 4.34 (q, 2H), 6.55 (s, 1H), 7.15 (d, 1H), 7.78 (dd, 1H), 8.75 (d, 1H).
MS (ES⁺): m/z 576 (M+NH₄).

Compound 35

2-[2-ethoxyl-5-(4-ethylpiperazinyl-1-sulphonyl)phenyl]-5-(pyrimidinyl-2)methyl-7-n-propyl-3,7-dihydropyrrolo[2,3-d]pyrimidin-4-one 4-ethoxyl-3-(5-morpholinomethyl-4-oxy-7-n-propyl-3,7-dihydropyrrolo[2,3-d]pyrimidin-2-yl)benzenesulfonylchloride (IB) was prepared from the reaction of 2-amino-3-cyano-4-(pyrimidinyl-2)methylpyrrole (IE) and 2-ethoxylbenzoyl chloride (IF) via the corresponding intermediates ID, IA, IG (IH) and IC. The resulting compound was reacted with 1-ethylpiperazine to give the titled compound.
¹H NMR (CDCl₃) δ: 0.90-1.00 (m, 6H), 1.60 (m, 6H), 1.75 (m, 2H), 2.37 (q, 2H), 2.53 (m, 4H), 3.06 (m, 4H), 4.01 (s, 2H), 4.07 (t, 2H), 4.35 (q, 2H), 6.69 (s, 1H), 7.11-7.15 (m, 2H), 7.77 (dd, 1H), 8.68-8.71 (m, 3H).
MS (ES⁺): m/z 569 (M+NH₄).

Compound 36

2-{2-ethoxyl-5-(4-ethylpiperazinyl-1-sulphonyl)phenyl}-5-methyl-7-allyl-3,7-dihydropyrrolo[2,3-d]pyrimidin-4-one 4-ethoxyl-3-(5-methyl-4-oxy-7-allyl-3,7-dihydropyrrolo[2,3-d]pyrimidin-2-yl)benzenesulfonylchloride (IB) was prepared from the reaction of 2-amino-3-cyano-4-methylpyrrole (IE) and 2-ethoxylbenzoyl chloride (IF) via the corresponding intermediates ID, IA, IG (IH) and IC. The resulting compound was reacted with 1-ethylpiperazine to give the titled compound.
¹H NMR (CDCl₃) δ: 1.00 (t, 3H), 1.65 (t, 3H), 2.37 (q, 2H), 2.41 (s, 3H), 2.50 (m, 4H), 3.09 (br, 4H), 4.31 (q, 2H), 4.95 (m, 2H), 4.96 (dd, 1H), 5.01 (dd, 1H), 5.68 (m, 1H), 6.61 (s, 1H), 7.11 (d, 1H), 7.82 (dd, 1H), 8.71 (d, 1H), 9.77 (br, 1H).
MS (ES⁺): m/z 503 (M+NH₄).

Example 2

Experiments of Penis Erection

In order to demonstrate efficacy of the compounds of formula I in treatment of functional impotence, the penis erection experiment was established by using the male rabbit as experimental model cross reference to Bischoff's method. (Bischoff E.; Schneider K, *International Journal of Impotence Research*, 2001, 13, 230 235)
The hydrochloride of 3,7-dihydropyrrolo[2,3-d]pyrimidin-4-one derivatives was dissolved into water, and injected to conscious-rabbits intravenously (i.v.) (0.1 mg-3 mg/kg). Erection was accessed by comparing the length of penis before and at 0, 30, 60, 90 and 120 minutes after intravenous administration of the above-mentioned agents. The results of typical compounds in this erectile experiment were listed in table 1.

TABLE 1 penis erection efficacy of
3,7-dihydropyrrolo[2,3-d]pyrimidin-4-one derivatives

| Compounds | Length of rabbit penis (mm) | | | | |
|---|---|---|---|---|---|
| | 0 min | 30 min | 60 min | 90 min | 120 min |
| Compound1-HCl | 8.3 | 5.7 | 5.3 | 2.0 | 1.3 |
| Compound1-2HCl | 1.3 | 3.0 | 2.0 | 1.0 | 1.0 |
| Compound6-2HCl | 0.0 | 5.3 | 2.7 | 1.7 | 0.0 |
| Compound8-2HCl | 2.7 | 1.7 | 1.3 | 0.7 | 0.0 |
| Compound19-2HCl | 1.7 | 4.0 | 4.3 | 4.0 | 0.0 |

*The data above were the average value of repeated experimental measurements of 3 rabbits.

The results showed that the above 3,7-dihydropyrrolo[2,3-d]pyrimidin-4-one derivatives had the good potential in treatment of functional erectile dysfunction with the characteristics of quick onset and prolonged effectiveness, especially the compound 1-1HCl.

Example 3

Experiments of the Effect of Single Administration on the Coitus Function of Male Rats After purchasing, the male rat and the estrogenized female rat were kept in the same cage for 2 days, and the male rat would acquire the sexual experiences. Then, the female rat was taken out of the cage, and the experiments began after the male rat stayed alone in a cage for 5 days. Each tested compound was orally administered in a dosage of 24 mg/kg, the positive group was administered with Sildenafil citrate (Viagra) in a dosage of 24 mg/kg, and the control group was administered with saline at the equal volume (0.1 ml/10 g). Fifty minutes after administration, the tested male rats were placed within a observation container (both the diameter and the height of the container were 24 cm), and the male rats adapted the new environment for 5 minutes. After that, two estrogenized female rats were placed into the container. The sexual behavior of the male rats in 20 minutes was observed under the non-interfering condition using Panasonic WVCP410/G monitor, the latent period of straddle, times of straddle, as well as the latent period of the coitus and times of the coitus. All the experiments were carried out at 21-24° C., and completed before 11:00 AM. The comparative results among the compounds of the invention, the blank and the positive control drug Sildenafil citrate were listed in Table 2.

The experimental results showed that all the indexes of sexual function of the rats were obviously enhanced after they were administered with compound 1-HCl, namely, the latent period of straddle and coitus were remarkably shortened, and the times of the coitus was obviously increased. And the effect of the compound 1-HCl was stronger than that of the Sildenafil citrate group, especially, the times of the coitus was much more than that of the positive control group (p<0.05). All the indexes of sexual function of the rats were also obviously enhanced after they were orally administered with Compound 6-HCl, in particular, the latent period of coitus was remarkably shorter than that of the positive control group. Therefore, the compound of the general formula I of the present invention can obviously enhance the sexual function of rats, and its effect was stronger than that of Sildenafil citrate.

TABLE 2

Effect of 3,7-dipyrrolo[2,3-d]pyrimidin-4-one derivatives on the indexes of sexual function of the male rats (average values ± standard deviations)

| Groups | Number of rats | the latent period of straddle (min) | times of straddle | the latent period of the coitus (min) | times of the coitus |
|---|---|---|---|---|---|
| saline | 17 | 8.9 ± 3.69 | 7.1 ± 3.62 | 16.2 ± 4.02 | 3.4 ± 4.64 |
| Compound1-HCl | 9 | 2.6 ± 1.13** | 7.6 ± 2.70 | 7.1 ± 5.62** | 13.1 ± 8.77**# |
| Compound6-HCl | 8 | 6.4 ± 3.07 | 8.0 ± 3.93 | 8.8 ± 5.85* | 9.0 ± 8.50 |
| Sildenafil citrate | 19 | 5.0 ± 4.74* | 12.7 ± 7.18 | 8.2 ± 4.02** | 8.2 ± 5.25* |

Compared with the group of saline,
*P < 0.05,
**P < 0.01;
Compared with the group of Sildenafil citrate,
P < 0.05.

Example 4

The Bioactivity Inhibiting Phosphodiesterase of Compounds of Formula I

The bioactivity inhibiting phosphodiesterase 5 (PDE5) of compounds of formula I was measured cross the reference of methods (Hidaka H, et al Biochim. Biochim. Biophys. Acta, 1976, 429, 485; Kim D-K, et al., Bioorg. Med. Chem. 2001, 9, 3013). The inhibiting activity of PDE5 was determined using SPA technique and the method of chemical fluorescence. The method was as follows: firstly, the reaction time curve and the enzyme concentration curve of PDE5 reaction system were determined by Microplate Scintillation & Luminescence Counter (TopCount Counter), by which the optimal reaction condition was determined. Under the optimized conditions, the inhibition experiments on PDE5 were carried out. The results showed that compound I had stronger inhibiting rate on phosphodiesterase 5 than that of sildenafil. For example, when the concentration of compound 1-HCl was $10^{-8}$ mol/L, the inhibiting rate of compound 1-HCl on PDE5 was 65.62%, but the inhibiting rate of sildenafil on PDE5 was 31.67%.

What is claimed is:

1. A method of treating male sexual (erectile) dysfunction or pulmonary hypertension, said method comprising administering to a patient in need thereof a composition comprising a compound of Formula I:

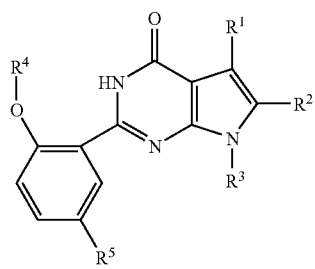

I wherein $R^1$ is $C_1$-$C_4$ branched or straight chain alkyl;

$R^2$ is H;

$R^3$ is H; $C_1$-$C_6$ branched or straight chain alkyl; $C_2$-$C_4$ alkenyl; or $C_2$-$C_4$ alkynyl;

$R^4$ is H; $C_1$-$C_6$ branched or straight chain alkyl; or $C_2$-$C_4$ alkenyl;

$R^5$ is $SO_2NR^{10}R^{11}$;

$R^8$ is H; or $C_1$-$C_6$ branched or straight chain alkyl;

$R^{10}$ and $R^{11}$ are each independently H; $C_1$-$C_{12}$ branched or straight chain alkyl; $C_1$-$C_3$ halogenated branched or straight chain alkyl; $C_2$-$C_6$ alkenyl; $C_2$-$C_6$ alkynyl or $C_3$-$C_6$ cycloalkyl; or $R^{10}$ and $R^{11}$ together with their attached nitrogen atom form a pyrrolinyl, pyrrolinone group, piperidyl, morpholinyl, or 4-N($R^8$)-piperazinyl, the said groups are optionally substituted with OH, CN, $CO_2R^8$, $C_1$-$C_4$ branched or straight chain alkyl, or $C_1$-$C_3$ alkoxyl;

or their pharmaceutically acceptable salts.

* * * * *